US008414525B2

(12) United States Patent
Wang

(10) Patent No.: US 8,414,525 B2
(45) Date of Patent: *Apr. 9, 2013

(54) DRUG RELEASING COATINGS FOR MEDICAL DEVICES

(75) Inventor: Lixiao Wang, Medina, MN (US)

(73) Assignee: Lutonix, Inc., New Hope, MN (US)

( * ) Notice: Subject to any disclaimer, the term of this patent is extended or adjusted under 35 U.S.C. 154(b) by 928 days.

This patent is subject to a terminal disclaimer.

(21) Appl. No.: 12/121,986

(22) Filed: May 16, 2008

(65) Prior Publication Data

US 2008/0255508 A1  Oct. 16, 2008

Related U.S. Application Data

(63) Continuation-in-part of application No. 11/942,452, filed on Nov. 19, 2007.

(60) Provisional application No. 60/860,084, filed on Nov. 20, 2006, provisional application No. 60/880,742, filed on Jan. 17, 2007, provisional application No. 60/897,427, filed on Jan. 25, 2007, provisional application No. 60/903,529, filed on Feb. 26, 2007, provisional application No. 60/926,850, filed on Apr. 30, 2007, provisional application No. 60/904,473, filed on Mar. 2, 2007, provisional application No. 60/981,380, filed on Oct. 19, 2007, provisional application No. 60/981, 384, filed on Oct. 19, 2007.

(51) Int. Cl.
*A61M 25/10* (2006.01)
*A61K 31/337* (2006.01)
*A61K 31/436* (2006.01)

(52) U.S. Cl.
USPC .................. 604/103.02; 514/291; 514/449

(58) Field of Classification Search .................. None
See application file for complete search history.

(56) References Cited

U.S. PATENT DOCUMENTS

| | | |
|---|---|---|
| 3,929,992 A | 12/1975 | Sehgal et al. |
| 3,993,749 A | 11/1976 | Sehgal et al. |
| 4,316,885 A | 2/1982 | Rakhit |
| 4,364,921 A | 12/1982 | Speck et al. |
| 4,921,483 A | 5/1990 | Wijay et al. |
| 5,023,262 A | 6/1991 | Caufield et al. |
| 5,023,263 A | 6/1991 | Von Burg |
| 5,023,264 A | 6/1991 | Caufield et al. |
| 5,026,607 A | 6/1991 | Kiezulas |
| 5,061,738 A | 10/1991 | Solomon et al. |
| 5,080,899 A | 1/1992 | Sturm et al. |
| 5,092,841 A | 3/1992 | Spears |
| 5,100,883 A | 3/1992 | Schiehser |
| 5,102,402 A | 4/1992 | Dror et al. |
| 5,102,876 A | 4/1992 | Caufield |
| 5,118,677 A | 6/1992 | Caufield |
| 5,118,678 A | 6/1992 | Kao et al. |
| 5,120,322 A | 6/1992 | Davis et al. |
| 5,120,725 A | 6/1992 | Kao et al. |
| 5,120,726 A | 6/1992 | Failli et al. |
| 5,120,727 A | 6/1992 | Kao et al. |
| 5,120,842 A | 6/1992 | Failli et al. |
| 5,130,307 A | 7/1992 | Failli et al. |
| 5,135,516 A | 8/1992 | Sahatjian et al. |
| 5,138,051 A | 8/1992 | Hughes et al. |
| 5,151,413 A | 9/1992 | Caufield et al. |
| 5,162,333 A | 11/1992 | Failli et al. |
| 5,164,299 A | 11/1992 | Failli et al. |
| 5,177,203 A | 1/1993 | Failli et al. |
| 5,193,447 A | 3/1993 | Kao |
| 5,196,596 A | 3/1993 | Abatjoglou |
| 5,199,951 A | 4/1993 | Spears |
| 5,221,670 A | 6/1993 | Caufield |
| 5,221,740 A | 6/1993 | Hughes |
| 5,233,036 A | 8/1993 | Hughes |
| 5,252,579 A | 10/1993 | Skotnicki et al. |
| 5,254,089 A | 10/1993 | Wang et al. |

(Continued)

FOREIGN PATENT DOCUMENTS

| | | |
|---|---|---|
| DE | 101 15 740 | 10/2002 |
| EP | 0 519 063 | 12/1992 |

(Continued)

OTHER PUBLICATIONS

Hershberger et al ("Calcitriol (1,25-dihydroxy cholecalciferol) Enhances Paclitaxel Antitumor Activity in Vitro and in Vivo and Accelerates Paclitaxel-Induced Apoptosis," Clin. Can. Res. 7:1043-1051 (Apr. 2001)).*

Scheller et al ("Paclitaxel Balloon Coating, a Novel Method for Prevention and Therapy of Restenosis," Circulation 2004; 110: 810-814).*

Charles et al., "Ceramide-Coated Balloon Catheters Limit Neointimal Hyperplasia after Stretch Injury in Carotid Arteries;" Circulation Research 2000; 87:282-288.

Hershberger et al., "Calcitriol (1, 25-dihydroxy cholecalciferol) Enhances Paclitaxel Antitumor Activity in Vitro and in Vivo and Accelerates Paclitaxel-Induced Apoptosis," Clin. Can. Res. 7: 1043-1051 (Apr. 2001).

(Continued)

*Primary Examiner* — Suzanne Ziska
(74) *Attorney, Agent, or Firm* — Dinsmore & Shohl LLP

(57) ABSTRACT

The invention relates to a medical device for delivering a therapeutic agent to a tissue. The medical device has a layer overlying the exterior surface of the medical device. The layer contains a therapeutic agent and an additive. In certain embodiments, the additive has a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. In embodiments, the additive is water-soluble. In further embodiments, the additive is at least one of a surfactant and a chemical compound, and the chemical compound has a molecular weight of from 80 to 750 or has more than four hydroxyl groups.

30 Claims, 2 Drawing Sheets

U.S. PATENT DOCUMENTS

| | | |
|---|---|---|
| 5,260,300 A | 11/1993 | Hu |
| 5,262,423 A | 11/1993 | Kao |
| 5,269,770 A | 12/1993 | Conway et al. |
| 5,302,584 A | 4/1994 | Kao et al. |
| 5,304,121 A | 4/1994 | Sahatjian |
| 5,324,261 A | 6/1994 | Amundson et al. |
| 5,346,893 A | 9/1994 | Failli et al. |
| 5,349,060 A | 9/1994 | Kao et al. |
| 5,362,718 A | 11/1994 | Skotnicki et al. |
| 5,370,614 A | 12/1994 | Amundson et al. |
| 5,373,014 A | 12/1994 | Failli et al. |
| 5,378,696 A | 1/1995 | Caufield |
| 5,378,836 A | 1/1995 | Kao et al. |
| 5,380,298 A | 1/1995 | Zabetakis et al. |
| 5,380,299 A | 1/1995 | Fearnot et al. |
| 5,385,908 A | 1/1995 | Nelson et al. |
| 5,385,909 A | 1/1995 | Nelson et al. |
| 5,385,910 A | 1/1995 | Ocain et al. |
| 5,387,680 A | 2/1995 | Nelson |
| 5,389,639 A | 2/1995 | Failli et al. |
| 5,391,730 A | 2/1995 | Skotnicki et al. |
| 5,411,967 A | 5/1995 | Kao et al. |
| 5,441,759 A | 8/1995 | Crouther et al. |
| 5,446,048 A | 8/1995 | Failli et al. |
| 5,463,048 A | 10/1995 | Skotnicki et al. |
| 5,464,650 A | 11/1995 | Berg et al. |
| 5,480,988 A | 1/1996 | Failli et al. |
| 5,480,989 A | 1/1996 | Kao et al. |
| 5,482,945 A | 1/1996 | Armstrong et al. |
| 5,489,680 A | 2/1996 | Failli et al. |
| 5,490,839 A | 2/1996 | Wang et al. |
| 5,491,231 A | 2/1996 | Nelson et al. |
| 5,496,276 A | 3/1996 | Wang et al. |
| 5,504,092 A | 4/1996 | Molnar-Kimber et al. |
| 5,504,204 A | 4/1996 | Failli et al. |
| 5,508,399 A | 4/1996 | Kao et al. |
| 5,509,899 A | 4/1996 | Fan et al. |
| 5,516,781 A | 5/1996 | Morris et al. |
| 5,525,348 A | 6/1996 | Whitbourne et al. |
| 5,525,610 A | 6/1996 | Caufield et al. |
| 5,530,007 A | 6/1996 | Kao et al. |
| 5,530,121 A | 6/1996 | Kao et al. |
| 5,532,355 A | 7/1996 | Skotnicki et al. |
| 5,536,729 A | 7/1996 | Waranis et al. |
| 5,559,121 A | 9/1996 | Harrison et al. |
| 5,559,227 A | 9/1996 | Failli et al. |
| 5,563,145 A | 10/1996 | Failli et al. |
| 5,563,146 A | 10/1996 | Morris |
| 5,567,709 A | 10/1996 | Skotnicki et al. |
| 5,573,518 A | 11/1996 | Haaga |
| 5,599,307 A | 2/1997 | Bacher et al. |
| 5,607,463 A | 3/1997 | Schwarz et al. |
| 5,609,629 A | 3/1997 | Fearnot et al. |
| 5,616,608 A | 4/1997 | Kinsella et al. |
| 5,632,772 A | 5/1997 | Alcime et al. |
| 5,674,192 A | 10/1997 | Sahatjian et al. |
| 5,674,287 A | 10/1997 | Slepian et al. |
| 5,679,400 A | 10/1997 | Tuch |
| 5,693,034 A | 12/1997 | Buscemi et al. |
| 5,698,582 A | 12/1997 | Bastart et al. |
| 5,702,754 A | 12/1997 | Zhong |
| 5,716,981 A | 2/1998 | Hunter et al. |
| 5,733,925 A | 3/1998 | Kunz et al. |
| 5,738,901 A | 4/1998 | Wang et al. |
| 5,752,930 A | 5/1998 | Rise et al. |
| 5,766,158 A | 6/1998 | Opolski |
| 5,776,184 A | 7/1998 | Tuch |
| 5,776,943 A | 7/1998 | Christians et al. |
| 5,780,462 A | 7/1998 | Lee et al. |
| 5,797,887 A | 8/1998 | Rosen et al. |
| 5,807,306 A | 9/1998 | Shapland et al. |
| 5,824,049 A | 10/1998 | Ragheb et al. |
| 5,827,289 A | 10/1998 | Reiley et al. |
| 5,843,089 A | 12/1998 | Sahatjian et al. |
| 5,865,814 A | 2/1999 | Tuch |
| 5,868,719 A | 2/1999 | Tsukernik |
| 5,869,127 A | 2/1999 | Zhong |
| 5,873,904 A | 2/1999 | Ragheb et al. |
| 5,879,697 A | 3/1999 | Ding et al. |
| 5,893,840 A | 4/1999 | Hull et al. |
| 5,919,145 A | 7/1999 | Sahatjian |
| 5,919,570 A | 7/1999 | Hostettler et al. |
| 5,922,730 A | 7/1999 | Hu et al. |
| 5,947,977 A | 9/1999 | Slepian et al. |
| 5,954,706 A | 9/1999 | Sahatjian |
| 5,977,163 A | 11/1999 | Li |
| 5,981,568 A | 11/1999 | Kunz et al. |
| 5,985,325 A | 11/1999 | Nagi |
| 5,989,591 A | 11/1999 | Nagi |
| 6,015,809 A | 1/2000 | Zhu et al. |
| 6,039,721 A | 3/2000 | Johnson et al. |
| 6,042,875 A | 3/2000 | Ding et al. |
| 6,046,230 A * | 4/2000 | Chung et al. ................ 514/449 |
| 6,050,980 A | 4/2000 | Wilson |
| 6,056,722 A | 5/2000 | Jayaraman |
| 6,074,659 A | 6/2000 | Kunz et al. |
| 6,096,070 A | 8/2000 | Ragheb et al. |
| 6,120,904 A | 9/2000 | Hostettler et al. |
| 6,129,705 A | 10/2000 | Grantz |
| 6,143,037 A | 11/2000 | Goldstein et al. |
| 6,146,358 A | 11/2000 | Rowe |
| 6,176,849 B1 | 1/2001 | Yang et al. |
| 6,218,016 B1 | 4/2001 | Tedeschi et al. |
| 6,221,467 B1 | 4/2001 | Nazarova et al. |
| 6,228,393 B1 | 5/2001 | DiCosmo et al. |
| 6,248,363 B1 | 6/2001 | Patel et al. |
| 6,261,630 B1 | 7/2001 | Nazarova et al. |
| 6,280,411 B1 | 8/2001 | Lennox |
| 6,294,192 B1 | 9/2001 | Patel et al. |
| 6,299,604 B1 | 10/2001 | Ragheb et al. |
| 6,299,980 B1 | 10/2001 | Shah et al. |
| 6,306,144 B1 | 10/2001 | Sydney et al. |
| 6,306,166 B1 | 10/2001 | Barry et al. |
| 6,312,406 B1 | 11/2001 | Jayaraman |
| 6,328,970 B1 | 12/2001 | Molnar-Kimber et al. |
| 6,331,547 B1 | 12/2001 | Zhu et al. |
| 6,335,029 B1 | 1/2002 | Kamath et al. |
| 6,364,856 B1 | 4/2002 | Ding et al. |
| 6,364,893 B1 | 4/2002 | Sahatjian et al. |
| 6,369,039 B1 | 4/2002 | Palasis et al. |
| 6,395,326 B1 | 5/2002 | Castro et al. |
| 6,409,716 B1 | 6/2002 | Sahatjian et al. |
| 6,419,692 B1 | 7/2002 | Yang et al. |
| 6,432,973 B1 | 8/2002 | Zhu et al. |
| 6,443,941 B1 | 9/2002 | Slepian et al. |
| 6,444,324 B1 | 9/2002 | Yang et al. |
| 6,458,138 B1 | 10/2002 | Sydney et al. |
| 6,506,408 B1 | 1/2003 | Palasis |
| 6,524,274 B1 | 2/2003 | Rosenthal et al. |
| 6,528,150 B2 | 3/2003 | Nazarova et al. |
| 6,544,544 B2 | 4/2003 | Hunter et al. |
| 6,571,125 B2 | 5/2003 | Thompson |
| 6,576,224 B1 | 6/2003 | Osbakken et al. |
| 6,589,215 B2 | 7/2003 | Yang et al. |
| 6,589,546 B2 | 7/2003 | Kamath et al. |
| 6,592,548 B2 | 7/2003 | Jayaraman |
| 6,610,035 B2 | 8/2003 | Yang et al. |
| 6,616,650 B1 | 9/2003 | Rowe |
| 6,656,156 B2 | 12/2003 | Yang et al. |
| 6,677,357 B2 | 1/2004 | Zhu et al. |
| 6,680,330 B2 | 1/2004 | Zhu et al. |
| 6,682,545 B1 | 1/2004 | Kester |
| 6,699,272 B2 | 3/2004 | Slepian et al. |
| 6,730,064 B2 | 5/2004 | Ragheb et al. |
| 6,774,278 B1 | 8/2004 | Ragheb et al. |
| 6,890,339 B2 | 5/2005 | Sahatjian et al. |
| 6,890,546 B2 | 5/2005 | Mollison et al. |
| 6,893,431 B2 | 5/2005 | Naimark et al. |
| 6,899,731 B2 | 5/2005 | Li et al. |
| 6,918,869 B2 | 7/2005 | Shaw et al. |
| 6,921,390 B2 | 7/2005 | Bucay-Couto et al. |
| 6,939,320 B2 | 9/2005 | Lennox |
| 6,958,153 B1 | 10/2005 | Ormerod et al. |
| 6,991,809 B2 | 1/2006 | Anderson |
| 6,997,949 B2 | 2/2006 | Tuch |
| 7,008,411 B1 | 3/2006 | Mandrusov et al. |
| 7,025,752 B2 | 4/2006 | Rice et al. |

| Patent/Publication | Date | Name |
|---|---|---|
| 7,048,714 B2 | 5/2006 | Richter |
| 7,056,550 B2 | 6/2006 | Davila et al. |
| 7,060,051 B2 | 6/2006 | Palasis |
| 7,066,904 B2 | 6/2006 | Rosenthal et al. |
| 7,077,859 B2 | 7/2006 | Sirhan et al. |
| 7,108,684 B2 | 9/2006 | Farnan |
| 7,144,419 B2 | 12/2006 | Cheng et al. |
| 7,153,957 B2 | 12/2006 | Chew et al. |
| 7,160,317 B2 | 1/2007 | McHale et al. |
| 7,163,555 B2 | 1/2007 | Dinh |
| 7,172,619 B2 | 2/2007 | Richter |
| 7,175,873 B1 | 2/2007 | Roorda et al. |
| 7,176,261 B2 | 2/2007 | Tijsma et al. |
| 7,179,251 B2 | 2/2007 | Palasis |
| 7,198,637 B2 | 4/2007 | Deshmukh et al. |
| 7,208,009 B2 | 4/2007 | Richter |
| 7,214,198 B2 | 5/2007 | Greco et al. |
| 7,226,586 B2 | 6/2007 | Fitzhugh et al. |
| 7,232,573 B1 | 6/2007 | Ding |
| 7,235,096 B1 | 6/2007 | Van Tassel et al. |
| 7,244,444 B2 | 7/2007 | Bates |
| 7,247,313 B2 | 7/2007 | Roorda et al. |
| 7,282,213 B2 | 10/2007 | Schroeder et al. |
| 7,285,304 B1 | 10/2007 | Hossainy et al. |
| 7,292,885 B2 | 11/2007 | Scott et al. |
| 7,294,329 B1 | 11/2007 | Ding |
| 7,306,580 B2 | 12/2007 | Paul et al. |
| 7,507,433 B2 | 3/2009 | Weber |
| 7,524,527 B2 | 4/2009 | Stenzel |
| 7,547,294 B2 | 6/2009 | Seward et al. |
| 2001/0002435 A1 | 5/2001 | Berg et al. |
| 2001/0018072 A1 | 8/2001 | Unger |
| 2001/0034363 A1 | 10/2001 | Li et al. |
| 2002/0010419 A1 | 1/2002 | Jayaraman |
| 2002/0039594 A1 | 4/2002 | Unger |
| 2002/0077684 A1 | 6/2002 | Clemens et al. |
| 2002/0082552 A1 | 6/2002 | Ding et al. |
| 2002/0095114 A1 | 7/2002 | Palasis |
| 2002/0098278 A1 | 7/2002 | Bates |
| 2002/0099332 A1 | 7/2002 | Slepian et al. |
| 2002/0102280 A1 | 8/2002 | Anderson |
| 2002/0138048 A1 | 9/2002 | Tuch |
| 2002/0151844 A1 | 10/2002 | Yang et al. |
| 2002/0183380 A1 | 12/2002 | Hunter |
| 2002/0192280 A1 | 12/2002 | Hunter |
| 2003/0004209 A1 | 1/2003 | Hunter et al. |
| 2003/0045587 A1 | 3/2003 | Anderson |
| 2003/0064965 A1 | 4/2003 | Richter |
| 2003/0100577 A1 | 5/2003 | Zhu et al. |
| 2003/0100886 A1 | 5/2003 | Segal et al. |
| 2003/0100887 A1 | 5/2003 | Scott et al. |
| 2003/0114477 A1 | 6/2003 | Zhu et al. |
| 2003/0114791 A1 | 6/2003 | Rosenthal et al. |
| 2003/0157032 A1 | 8/2003 | Cavaillon et al. |
| 2003/0157161 A1 | 8/2003 | Hunter |
| 2003/0207936 A1 | 11/2003 | Chen |
| 2003/0216699 A1 | 11/2003 | Falotico |
| 2003/0235602 A1 | 12/2003 | Schwarz |
| 2004/0018296 A1 | 1/2004 | Castro et al. |
| 2004/0037886 A1 | 2/2004 | Hsu |
| 2004/0062810 A1 | 4/2004 | Hunter |
| 2004/0073284 A1 | 4/2004 | Bates et al. |
| 2004/0076672 A1 | 4/2004 | Hunter |
| 2004/0077677 A1 | 4/2004 | Ashraf et al. |
| 2004/0087902 A1 | 5/2004 | Richter |
| 2004/0127551 A1* | 7/2004 | Zhang et al. ............... 514/449 |
| 2004/0156816 A1 | 8/2004 | Anderson |
| 2004/0167152 A1 | 8/2004 | Rubino et al. |
| 2004/0176339 A1 | 9/2004 | Sherman et al. |
| 2004/0197408 A1 | 10/2004 | Gravett |
| 2004/0201117 A1 | 10/2004 | Anderson |
| 2004/0202712 A1 | 10/2004 | Lambert et al. |
| 2004/0219214 A1 | 11/2004 | Gravett |
| 2004/0224001 A1 | 11/2004 | Pacetti et al. |
| 2004/0224003 A1 | 11/2004 | Schultz |
| 2004/0225077 A1 | 11/2004 | Gravett |
| 2004/0230176 A1 | 11/2004 | Shanahan et al. |
| 2004/0258662 A1 | 12/2004 | Gibbons, Jr. et al. |
| 2005/0025802 A1 | 2/2005 | Richard et al. |
| 2005/0038409 A1 | 2/2005 | Segal et al. |
| 2005/0049271 A1 | 3/2005 | Benjamin et al. |
| 2005/0054978 A1 | 3/2005 | Segal et al. |
| 2005/0055078 A1 | 3/2005 | Campbell |
| 2005/0080477 A1 | 4/2005 | Sydney et al. |
| 2005/0100580 A1 | 5/2005 | Osborne et al. |
| 2005/0101522 A1 | 5/2005 | Speck et al. |
| 2005/0123582 A1 | 6/2005 | Sung et al. |
| 2005/0152983 A1 | 7/2005 | Ashraf et al. |
| 2005/0159704 A1 | 7/2005 | Scott et al. |
| 2005/0171596 A1 | 8/2005 | Furst et al. |
| 2005/0182361 A1 | 8/2005 | Lennox |
| 2005/0186244 A1 | 8/2005 | Hunter et al. |
| 2005/0191323 A1 | 9/2005 | Chen |
| 2005/0191333 A1 | 9/2005 | Hsu |
| 2005/0209664 A1 | 9/2005 | Hunter et al. |
| 2005/0222191 A1 | 10/2005 | Falotico et al. |
| 2005/0234086 A1 | 10/2005 | Gu et al. |
| 2005/0234087 A1 | 10/2005 | Gu et al. |
| 2005/0234234 A1 | 10/2005 | Gu et al. |
| 2005/0238584 A1 | 10/2005 | Annapragada et al. |
| 2005/0239178 A1 | 10/2005 | Ruppen et al. |
| 2005/0250672 A9 | 11/2005 | Speck et al. |
| 2005/0251249 A1 | 11/2005 | Sahatjian et al. |
| 2005/0256564 A1 | 11/2005 | Yang et al. |
| 2005/0272758 A1 | 12/2005 | Bayever et al. |
| 2005/0278021 A1 | 12/2005 | Bates et al. |
| 2006/0020243 A1 | 1/2006 | Speck et al. |
| 2006/0020331 A1 | 1/2006 | Bates et al. |
| 2006/0040971 A1 | 2/2006 | Zhu et al. |
| 2006/0045901 A1 | 3/2006 | Weber et al. |
| 2006/0051392 A1 | 3/2006 | Heruth et al. |
| 2006/0052744 A1 | 3/2006 | Weber |
| 2006/0067977 A1* | 3/2006 | Labrecque et al. ............ 424/426 |
| 2006/0094745 A1 | 5/2006 | R. Ruffalo, Jr. |
| 2006/0112536 A1 | 6/2006 | Herweck et al. |
| 2006/0121545 A1 | 6/2006 | Molnar-Kimber et al. |
| 2006/0127445 A1 | 6/2006 | Hunter |
| 2006/0135549 A1 | 6/2006 | Graziani et al. |
| 2006/0135550 A1 | 6/2006 | Graziani et al. |
| 2006/6121117 | 6/2006 | Hunter |
| 2006/0165753 A1 | 7/2006 | Richard |
| 2006/0183766 A1 | 8/2006 | Boni et al. |
| 2006/0184236 A1 | 8/2006 | Jones et al. |
| 2006/0188543 A1 | 8/2006 | Feng |
| 2006/0199834 A1 | 9/2006 | Zhu |
| 2006/0199954 A1 | 9/2006 | Shaw et al. |
| 2006/0224237 A1 | 10/2006 | Furst et al. |
| 2006/0230476 A1 | 10/2006 | Atanasoka et al. |
| 2006/0240113 A1 | 10/2006 | Hunter |
| 2006/0257444 A1 | 11/2006 | Tropsha et al. |
| 2006/0257445 A1 | 11/2006 | Tropsha et al. |
| 2006/0282114 A1 | 12/2006 | Barone |
| 2007/0003629 A1 | 1/2007 | Hunter |
| 2007/0003630 A1 | 1/2007 | Hunter |
| 2007/0020308 A1 | 1/2007 | Richard et al. |
| 2007/0020380 A1 | 1/2007 | Ding |
| 2007/0032694 A1 | 2/2007 | Dinkelborg et al. |
| 2007/0050010 A1 | 3/2007 | Bates et al. |
| 2007/0059434 A1 | 3/2007 | Roorda et al. |
| 2007/0065484 A1 | 3/2007 | Chudzik et al. |
| 2007/0073385 A1 | 3/2007 | Schaeffer et al. |
| 2007/0077347 A1 | 4/2007 | Richter |
| 2007/0078446 A1 | 4/2007 | Lavelle |
| 2007/0078513 A1 | 4/2007 | Campbell et al. |
| 2007/0117925 A1 | 5/2007 | Strickler et al. |
| 2007/0128118 A1 | 6/2007 | Yu et al. |
| 2007/0142772 A1 | 6/2007 | Deshmukh et al. |
| 2007/0142905 A1 | 6/2007 | Hezi-Yamit et al. |
| 2007/0150043 A1 | 6/2007 | Richter |
| 2007/0150047 A1 | 6/2007 | Ruane et al. |
| 2007/0161967 A1 | 7/2007 | Fischer, Jr. et al. |
| 2007/0162103 A1 | 7/2007 | Case et al. |
| 2007/0167735 A1 | 7/2007 | Zhong et al. |
| 2007/0168012 A1 | 7/2007 | Ragheb et al. |
| 2007/0184083 A1 | 8/2007 | Coughlin |
| 2007/0190103 A1 | 8/2007 | Hossainy et al. |
| 2007/0191934 A1 | 8/2007 | Blakstvedt et al. |
| 2007/0198080 A1 | 8/2007 | Ding et al. |

| | | | | | | |
|---|---|---|---|---|---|---|
| 2007/0212386 A1 | 9/2007 | Patravale et al. | | EP | 0 879 595 A2 | 11/1998 |
| 2007/0212394 A1 | 9/2007 | Reyes et al. | | EP | 1 118 325 A2 | 7/2001 |
| 2007/0218246 A1 | 9/2007 | Ding | | EP | 1 372 737 A2 | 1/2004 |
| 2007/0219642 A1 | 9/2007 | Richter | | EP | 1 468 660 A2 | 10/2004 |
| 2007/0225799 A1 | 9/2007 | Doty | | EP | 1 510 220 A1 | 3/2005 |
| 2007/0237803 A1 | 10/2007 | Cheng et al. | | EP | 1 539 266 A1 | 6/2005 |
| 2007/0244284 A1 | 10/2007 | Cheng et al. | | EP | 1 539 267 | 6/2005 |
| 2007/0244548 A1 | 10/2007 | Myers et al. | | EP | 1 576 970 A1 | 9/2005 |
| 2007/0264307 A1 | 11/2007 | Chen et al. | | EP | 1 586 338 A2 | 10/2005 |
| 2007/0265565 A1 | 11/2007 | Johnson | | EP | 1 649 853 | 4/2006 |
| 2007/0276466 A1 | 11/2007 | Lavelle et al. | | EP | 1 666 070 A1 | 6/2006 |
| 2007/0282422 A1 | 12/2007 | Biggs et al. | | EP | 1 666 071 B1 | 6/2006 |
| 2007/0286814 A1 | 12/2007 | Sawant et al. | | EP | 1 669 092 A1 | 6/2006 |
| 2007/0298069 A1 | 12/2007 | Bucay-Couto et al. | | EP | 1 857 127 | 11/2007 |
| 2008/0021385 A1 | 1/2008 | Barry et al. | | EP | 1 913 962 A1 | 4/2008 |
| 2008/0038307 A1 | 2/2008 | Hoffmann | | EP | 1 970 185 | 9/2008 |
| 2008/0082552 A1 | 4/2008 | Krishnaswamy | | EP | 2 127 617 | 12/2009 |
| 2008/0102033 A1* | 5/2008 | Speck et al. ............ 424/9.3 | | WO | WO 92/11890 A1 | 7/1992 |
| 2008/0102034 A1 | 5/2008 | Speck et al. | | WO | WO 94/07484 | 4/1994 |
| 2008/0114331 A1 | 5/2008 | Holman et al. | | WO | WO 94/07529 | 4/1994 |
| 2008/0140002 A1 | 6/2008 | Ramzipoor et al. | | WO | WO 94/16706 | 8/1994 |
| 2008/0215137 A1 | 9/2008 | Epstein et al. | | WO | WO 94/26291 | 11/1994 |
| 2008/0255508 A1 | 10/2008 | Wang | | WO | WO 95/03036 | 2/1995 |
| 2008/0255509 A1 | 10/2008 | Wang | | WO | WO 95/03795 | 2/1995 |
| 2008/0255510 A1 | 10/2008 | Wang | | WO | WO 96/25176 | 8/1996 |
| 2008/0255658 A1 | 10/2008 | Cook et al. | | WO | WO 96/39949 | 12/1996 |
| 2008/0262412 A1 | 10/2008 | Atanasoska et al. | | WO | WO 97/25977 | 7/1997 |
| 2008/0274159 A1 | 11/2008 | Shultz | | WO | WO 98/02114 | 1/1998 |
| 2008/0274266 A1 | 11/2008 | Davis et al. | | WO | WO 98/14174 | 4/1998 |
| 2008/0276935 A1 | 11/2008 | Wang | | WO | WO 98/30249 | 7/1998 |
| 2008/0317827 A1 | 12/2008 | Wright et al. | | WO | WO 98/36784 | 8/1998 |
| 2009/0011116 A1 | 1/2009 | Herweck et al. | | WO | WO 98/57671 A2 | 12/1998 |
| 2009/0047414 A1 | 2/2009 | Corbeil et al. | | WO | WO 99/08729 | 2/1999 |
| 2009/0069883 A1 | 3/2009 | Ding et al. | | WO | WO 00/21584 | 4/2000 |
| 2009/0076448 A1 | 3/2009 | Cosigny et al. | | WO | WO 00/32238 | 6/2000 |
| 2009/0098176 A1 | 4/2009 | Helmus et al. | | WO | WO 00/32267 | 6/2000 |
| 2009/0105686 A1 | 4/2009 | Snow et al. | | WO | WO 00/44414 | 8/2000 |
| 2009/0105687 A1 | 4/2009 | Deckman et al. | | WO | WO 00/45744 A1 | 8/2000 |
| 2009/0136560 A1 | 5/2009 | Bates et al. | | WO | WO 01/24866 | 4/2001 |
| 2009/0181937 A1 | 7/2009 | Faucher et al. | | WO | WO 02/076509 A2 | 10/2002 |
| 2009/0182273 A1 | 7/2009 | Johnson | | WO | WO 2004/006976 | 1/2004 |
| 2009/0187144 A1 | 7/2009 | Jayaraman | | WO | WO 2004/026357 A1 | 4/2004 |
| 2009/0208552 A1 | 8/2009 | Faucher et al. | | WO | WO 2004/028582 A2 | 4/2004 |
| 2009/0215882 A1 | 8/2009 | Bouzada et al. | | WO | WO 2004/028610 | 4/2004 |
| 2009/0227948 A1 | 9/2009 | Chen et al. | | WO | WO 2005/011769 A2 | 2/2005 |
| 2009/0227949 A1 | 9/2009 | Knapp et al. | | WO | WO 2006/023859 A1 | 3/2006 |
| 2009/0238854 A1 | 9/2009 | Pacetti et al. | | WO | WO 2006/081210 A2 | 8/2006 |
| 2009/0246252 A1 | 10/2009 | Arps et al. | | WO | WO 2006/101573 A1 | 9/2006 |
| 2009/0324682 A1 | 12/2009 | Popowski | | WO | WO 2006/124647 A1 | 11/2006 |
| 2010/0030183 A1 | 2/2010 | Toner et al. | | WO | WO 2007/047416 A2 | 4/2007 |
| 2010/0055294 A1 | 3/2010 | Wang et al. | | WO | WO 2007/079560 A2 | 7/2007 |
| 2010/0063570 A1 | 3/2010 | Pacetti et al. | | WO | WO 2007/134239 A2 | 11/2007 |
| 2010/0068186 A1 | 3/2010 | Michal et al. | | WO | WO 2007/139931 A2 | 12/2007 |
| 2010/0069838 A1 | 3/2010 | Weber et al. | | WO | WO 2007/149161 A2 | 12/2007 |
| 2010/0069879 A1 | 3/2010 | Michal et al. | | WO | WO 2008/003298 A2 | 1/2008 |
| 2010/0081992 A1 | 4/2010 | Ehrenreich et al. | | WO | WO 2008/063576 A2 | 5/2008 |
| 2010/0087783 A1 | 4/2010 | Weber et al. | | WO | WO 2008/086794 | 7/2008 |
| 2010/0198150 A1 | 8/2010 | Michal et al. | | WO | WO 2008/114585 | 9/2008 |
| 2010/0198190 A1 | 8/2010 | Michal et al. | | | | |
| 2010/0272773 A1 | 10/2010 | Kangas et al. | | | | |
| 2010/0285085 A1 | 11/2010 | Stankus et al. | | | | |
| 2010/0324645 A1 | 12/2010 | Stankus et al. | | | | |
| 2010/0331816 A1 | 12/2010 | Dadino et al. | | | | |
| 2011/0054396 A1 | 3/2011 | Kangas et al. | | | | |
| 2011/0060275 A1 | 3/2011 | Christiansen | | | | |
| 2011/0129514 A1 | 6/2011 | Hossainy et al. | | | | |
| 2011/0137243 A1 | 6/2011 | Hossainy et al. | | | | |
| 2011/0143014 A1 | 6/2011 | Stankus et al. | | | | |
| 2011/0144577 A1 | 6/2011 | Stankus et al. | | | | |
| 2011/0144578 A1 | 6/2011 | Pacetti et al. | | | | |
| 2011/0152906 A1 | 6/2011 | Escudero et al. | | | | |
| 2011/0152907 A1 | 6/2011 | Escudero et al. | | | | |
| 2011/0178503 A1 | 7/2011 | Kangas | | | | |
| 2011/0190863 A1 | 8/2011 | Ostroot et al. | | | | |

FOREIGN PATENT DOCUMENTS

| | | | |
|---|---|---|---|
| EP | | 0 702 557 A1 | 3/1996 |
| EP | | 0 706 376 B2 | 4/1996 |
| EP | | 0 711 158 A1 | 5/1996 |

OTHER PUBLICATIONS

International Search Report for International Application No. PCT/US2008/006348, dated Jan. 28, 2009.
International Search Report for International Application No. PCT/US2008/006415, dated Nov. 24, 2008.
International Search Report for International Application No. PCT/2007/024108, Nov. 20, 2008.
International Search Report for International Application No. PCT/2008/006417, Nov. 24, 2008.
International Search Report for International Application No. PCT/2009/004868, May 21, 2010.
Office Action in co-pending U.S. Appl. No. 11/942,452, dated Apr. 29, 2010.
Office Action in co-pending U.S. Appl. No. 11/942,459, dated Apr. 20, 2010.
Scheller et al., Paclitaxel Balloon Coating, a Novel Method for Prevention and Therapy of Restenosis, Circulation 2004; 110;810-814; originally published online Aug. 9, 2004.
European Search Report for EP 09156858, Jul. 21, 2009.

European Search Report for EP 09160605, Jul. 20, 2009.
European Search Report for EP 10168411, Nov. 30, 2010.
European Search Report for EP 10168412, Nov. 30, 2010.
European Search Report for EP 10189393, Apr. 4, 2011.
Office Action in U.S. Appl. No. 12/135,648, dated Feb. 18, 2011.
Office Action in U.S. Appl. No. 11/942,459, dated Jul. 19, 2011.
Office Action in U.S. Appl. No. 12/123,951, dated Jun. 16, 2011.
Office Action in U.S. Appl. No. 12/123,956, dated Jun. 28, 2011.
Office Action in U.S. Appl. No. 12/135,648, dated Jul. 13, 2011.
Office Action in U.S. Appl. No. 12/731,835, dated Jul. 6, 2011.
Office Action in U.S. Appl. No. 13/042,213, dated Jul. 8, 2011.
Office Action in U.S. Appl. No. 13/042,218, dated Aug. 17, 2011.
International Search Report for International Application No. PCT/2007/024108, dated Aug. 7, 2008.
International Search Report for International Application No. PCT/US2008/006415, dated May 20, 2008.
International Search Report for International Application No. PCT/US2008/006348, dated May 16, 2008.
International Search Report for International Application No. PCT/US2008/006417, dated May 20, 2008.
International Search Report for International Application No. PCT/2008/007177, Sep. 16, 2008.
International Search Report for International Application No. PCT/2007/024116, dated Nov. 2, 2008.
Li J. Chiang et al., "Potent inhibition of tumor survival in vivo by β-lapachone plus taxol: Combining drugs imposes different artificial checkpoints," PNAS, vol. 96, No. 23, Nov. 9, 1999, at pp. 13369-13374.
D.M. Jackson et al., "Current usage of contract agents, anticoagulant and antiplatelet drugs in angiography and angioplasty in the UK," Department of Diagnostic Radiology, Hammersmith Hospital, London, UK, Clinical Radiology (1995), 50, pp. 699-704.
Seymour R. Halpin SF et al., "Corticosteroid prophylaxis for patients with increased risk of adverse reactions to intravascular contrast agents: a survey of current practice in the UK," Department of Radiology, University Hospital of Wales, Heath Park, Cardiff, Clinical Radiology (1994), 49, pp. 791-795.
Toshimitsu Konno, M.D., et al., "Selective targeting of anti-cancer drug and simultaneous imaging enhancement in solid tumors by arterially administered lipid contrast medium," Cancer 54:2367-2374, 1984.
Ken Iwai, et al., "Use of oily contrast medium for selective drug targeting to sumor: Enhanced therapeutic effect and X-ray image," Cancer Research, 44, 2115-2121, May 1994.
Journal of Microencapsulation, 17, 6, Nov. 2, 2000, p. 789-799.
New England Journal of Medicine, 1995, 332: 1004-1014.
Chun Li, et al, "Synthesis, Biodistribution and Imaging Properties of Indium-111-DTPA-Paclitaxel in Mice Bearing Mammary Tumors," The Journal of Nuclear Medicine, vol. 38, No. 7, Jul. 1997, 1042-1047.
D. M. Long et al., "Perflurocarbon Compounds As X-Ray Contrast Media In The Lungs," Bulletin de la Societe Internationale De Chirurgie, vol. 2, 1975, 137-141.
Herdeg et al., "Paclitaxel: Ein Chemotherapeuticum zum Restenoseprophylaxe? Experimentell Untersuchungen in vitro und in vivo," Z Kardiol, vol. 89 (2000) pp. 390-397.
Prashant N. Chhajed et al., "Patterns of Pulmonary Complications Associated with Sirolimus," Respiration: International Review of Thoracic Diseases, vol. 73, No. 3, Mar. 2006, at pp. 367-374.
Laure Champion et al., "Brief Communication: Sirolimus-Associated Pneumonitis: 24 Cases in Renal Transplant Recipients," Annals of Internal Medicine, vol. 144, No. 7, Apr. 4, 2006, at pp. 505-509.
Gyula Ostoros et al., "Paclitaxel Induced Pulmonary Fibrosis," Lung Cancer, Elsevier, Amsterdam, NL, vol. 41, Aug. 1, 2003, at p. S280.
Gyula Ostoros et al., "Fatal Pulmonary Fibrosis Induced Paclitaxel: A Case Report and Review of the Literature," International Journal of Gynecological Cancer, vol. 16, Suppl. 1, Jan. 2006, at pp. 391-393.
Baumbach et al., "Local Drug Delivery: Impact of Pressure Substance Characteristics, and Stenting on Drug Transfer Into the Arterial Wall," Catheterization and Cardiovascular Interventions, vol. 47, pp. 102-106 (1999).
Charles et al., "Ceramide-Coated Balloon Catheters Limit Neointimal Hyperplasia After Stretch Injury in Carotid Arteries," Circulation Research published by the American Heart Association, 87, pp. 282-288 (2000).
English Language Abstract for EP 1 372 737 A2, Jan. 20, 2004.
English Language Abstract for EP 1 539 266 A1, Jun. 15, 2005.
English Language Abstract for EP 1 666 070 A1, Jun. 7, 2006.
English Language Abstract for EP 1 666 071 A1, Jun. 7, 2006.
English Language Abstract for EP 1 669 092 A1, Jun. 14, 2006.
English Language Abstract for WO 02/076509, Oct. 3, 2002.
English Language Abstract for WO 2004/028582, Apr. 8, 2004.
English Language Abstract for WO 2004/028610, Apr. 8, 2004.
English Language Abstract for WO 2008/003298 A2, Jan. 10, 2008.
"Literature Alerts", Journal of Microencapsulation, vol. 17, No. 6, pp. 789-799 (2000).
Baron, J.H., et al., "In vitro evaluation of c7E3-Fab (ReoPro) eluting polymer-coated coronary stents." Cardiovascular Research, 46 (2000) pp. 585-594.
Creel, C.J., et al., "Arterial Paclitaxel Distribution and Deposition", Circ Res, vol. 86, pp. 879-884 (2000).
International Search Report for International Application No. PCT/US2009/004868, Jan. 4, 2010.
International Search Report for International Application No. PCT/US2010/028599, dated Dec. 21, 2010.
Kandarpa, K., et al., "Mural Delivery of Iloprost with Use of Hydrogel-coated Balloon Catheters Suppresses Local Platelet Aggregation." J. Vasc. Interv. Radiol. 8, pp. 997-1004, Nov./Dec. 1997.
Kandarpa, K., et al., "Site-specific Delivery of Iloprost during Experimental Angioplasty Suppresses Smooth Muscle Cell Proliferation." J. Vasc. Interv. Radiol. 9, pp. 487-493, (1998).
Leo, A., et al., "Partition coefficients and their uses." Chem Rev, vol. 71 (6), pp. 525-537 (1971).
Mitchel, J.F., et al., "Inhibition of Platelet Deposition and Lysis of Intracoronary Thrombus During Balloon Angioplasty Using Urokinase-Coated Hydrogel Balloons." Circulation 90, (Oct. 1994), pp. 1979-1988.
Office Action in co-pending U.S. Appl. No. 11/942,452, dated Oct. 13, 2010.
Office Action in co-pending U.S. Appl. No. 11/942,459, dated Sep. 27, 2010.
Office Action in co-pending U.S. Appl. No. 12/135,648, dated Feb. 18, 2011.
PPD, "Evaluation of Butanol-Buffer Distribution Properties of C6-Ceraminde." PPD Project No. 7557-001, Aug. 20, 2008, pp. 1-14.
Rowinsky, E. K., et al., "Drug therapy: paclitaxel (taxol)", Review Article, N Engl J Med, vol. 332, No. 15, pp. 1004-1014, (1995).
Sangster, James, "Octanol-Water Partition Coefficients: Fundamentals and Physical Chemistry", Wiley Series in Solution Chemistry vol. 2, Chichester: John Wiley & Sons, vol. 2, Chapter 1 (1997).
Yushmanov, et al., "Dipyridamole Interacts with the Polar Part of Cationic Reversed Micelles in Chloroform: 1H NMR and ESR Evidence", J. Colloid Interface Sci., vol. 191(2), pp. 384-390 (1997).

* cited by examiner ures, which are particularly detrimental when drug is supposed to be rapidly released, and hyperplasia and restenosis areas that are

DRUG RELEASING COATINGS FOR MEDICAL DEVICES

CROSS REFERENCE TO RELATED APPLICATIONS

This application is a continuation-in-part of application Ser. No. 11/942,452, filed Nov. 19, 2007, which claims the benefit of priority of U.S. Provisional Application No. 60/860,084, filed on Nov. 20, 2006, U.S. Provisional Application No. 60/880,742, filed Jan. 17, 2007, U.S. Provisional Application No. 60/897,427, filed on Jan. 25, 2007, U.S. Provisional Application No. 60/903,529 filed on Feb. 26, 2007, U.S. Provisional Application No. 60/904,473 filed Mar. 2, 2007, U.S. Provisional Application No. 60/926,850 filed Apr. 30, 2007, U.S. Provisional Application No. 60/981,380 filed Oct. 19, 2007, and U.S. Provisional Application No. 60/981,384 filed Oct. 19, 2007, the disclosures of all of which are incorporated by reference herein.

FIELD OF THE INVENTION

Embodiments of the present invention relate to coated medical devices, and particularly to coated balloon catheters, and their use for rapidly delivering a therapeutic agent to particular tissue or body lumen, for treatment of disease and particularly for reducing stenosis and late lumen loss of a body lumen. Embodiments of the present invention also relate to methods of manufacturing these medical devices, the coatings provided on these medical devices, the solutions for making those coatings, and methods for treating a body lumen such as the vasculature, including particularly arterial vasculature, for example, using these coated medical devices.

BACKGROUND OF THE INVENTION

It has become increasingly common to treat a variety of medical conditions by introducing a medical device into the vascular system or other lumen within a human or veterinary patient such as the esophagus, trachea, colon, biliary tract, or urinary tract. For example, medical devices used for the treatment of vascular disease include stents, catheters, balloon catheters, guide wires, cannulas and the like. While these medical devices initially appear successful, the benefits are often compromised by the occurrence of complications, such as late thrombosis, or recurrence of disease, such as stenosis (restenosis), after such treatment.

Restenosis, for example, involves a physiological response to the vascular injury caused by angioplasty. Over time, de-endotheliaziation and injury to smooth muscle cells results in thrombus deposition, leukocyte and macrophage infiltration, smooth muscle cell proliferation/migration, fibrosis and extracellular matrix deposition. Inflammation plays a pivotal role linking early vascular injury to the eventual consequence of neointimal growth and lumen compromise. In balloon-injured arteries, leukocyte recruitment is confined to early neutrophil infiltration, while in stented arteries, early neutrophil recruitment is followed by prolonged macrophage accumulation. The widespread use of coronary stents has altered the vascular response to injury by causing a more intense and prolonged inflammatory state, due to chronic irritation from the implanted foreign body, and in the case of drug eluting stents (DES), from insufficient biocompatibility of the polymer coating.

Over the past several years, numerous local drug delivery systems have been developed for the treatment and/or the prevention of restenosis after balloon angioplasty or stenting. Examples include local drug delivery catheters, delivery balloon catheters, and polymeric drug coated stents. Given that many diseases affect a specific local site or organ within the body, it is advantageous to preferentially treat only the affected area. This avoids high systemic drug levels, which may result in adverse side effects, and concentrates therapeutic agents in the local area where they are needed. By treating just the diseased tissue, the total quantity of drug used may be significantly reduced. Moreover, local drug delivery may allow for the use of certain effective therapeutic agents, which have previously been considered too toxic or non-specific to use systemically.

One example of a local delivery system is a drug eluting stent (DES). The stent is coated with a polymer into which drug is impregnated. When the stent is inserted into a blood vessel, the polymer degrades and the drug is slowly released. The slow release of the drug, which takes place over a period of weeks to months, has been reported as one of the main advantages of using DES. However, while slow release may be advantageous in the case where a foreign body, such as a stent, is deployed, which is a source of chronic irritation and inflammation, if a foreign body is not implanted it is instead advantageous to rapidly deliver drug to the vascular tissue at the time of treatment to inhibit inflammation and cellular proliferation following acute injury. Thus, a considerable disadvantage of a DES, or any other implanted medical device designed for sustained release of a drug, is that the drug is incapable of being rapidly released into the vessel.

Additionally, while drug-eluting stents were initially shown to be an effective technique for reducing and preventing restenosis, recently their efficacy and safety have been questioned. A life-threatening complication of the technology, late thrombosis, has emerged as a major concern. Drug eluting stents cause substantial impairment of arterial healing, characterized by a lack of complete re-endothelialization and a persistence of fibrin when compared to bare metal stents (BMS), which is understood to be the underlying cause of late DES thrombosis. Concerns have also been raised that the polymeric matrix on the stent in which the anti-proliferative drug is embedded might exacerbate inflammation and thrombosis, since the polymers used are not sufficiently biocompatible. These polymeric systems are designed to facilitate long-term sustained release of drug over a period of days, months, or years, not over a period of seconds or minutes. These polymeric drug coatings of medical devices do not release the polymer, which remains on the device even after drug is released. Even if biodegradable polymers are used, polymer and drug are not released at the same time. Rapid release of drug, an intent of embodiments of the present invention, from these polymeric systems is not possible. Thus, combining a therapeutic agent with a polymer in a medical device coating may have significant disadvantages.

Another important limitation of the DES is that the water insoluble drugs are not evenly distributed in the polymeric matrix of the coating. Furthermore, drug and polymer are concentrated on the struts of the stent, but not in gaps between the struts. The non-uniform distribution of drug causes non-uniform drug release to the tissue of the vessel walls. This may cause tissue damage and thrombosis in areas exposed to excess drug and hyperplasia and restenosis areas that are undertreated. Thus, there is a need to improve the uniformity of drug delivery to target tissues by improving drug solubility in coatings of medical devices by increasing the drug's compatibility with carriers in the coatings, such as a polymeric matrix, thereby eliminating or reducing the size of drug crystal particles in the polymeric matrix or other coating to create a uniform drug distribution in the drug coating on the medical device.

Yet another important limitation of the DES is that only a limited amount of an active agent can be loaded into the relatively small surface area of the stent.

Non-stent based local delivery systems, such as balloon catheters, have also been effective in the treatment and prevention of restenosis. The balloon is coated with an active agent, and when the blood vessel is dilated, the balloon is pressed against the vessel wall to deliver the active agent. Thus, when balloon catheters are used, it is advantageous for the drug in the coating to be rapidly released and absorbed by blood vessel tissues. Any component of the coating that inhibits rapid release, such as a lipid or polymer or an encapsulating particle, is necessarily disadvantageous to the intended use of the balloon catheter, which is inflated for a very brief period of time and then removed from the body.

Hydrophilic drugs, such as heparin, have been reported to be deliverable by polymeric hydrogel coated balloon catheters. However, a polymeric hydrogel coating can not effectively deliver water insoluble drugs (such as paclitaxel and rapamycin), because they can not mix with the hydrogel coating. Furthermore, as drug is released, the cross-linked polymeric hydrogel remains on the balloon after drug is released. The iodine contrast agent iopromide has been used with paclitaxel to coat balloon catheters and has some success in treatment of restenosis. It was reported that contrast agent improves adhesion of paclitaxel to the balloon surface. However, iodinated contrast agents suffer from several well known disadvantages. When used for diagnostic procedures, they may have complication rates of 5-30%. These agents are associated with the risk of bradycardia, ventricular arrthymia, hypotension, heart block, sinus arrest, sinus tachycardia, and fibrillation. Iodine contrast agents may also induce renal failure, and as a result there are significant efforts to remove these contrast agents from the vascular system after diagnostic procedures.

In addition, the Food and Drug Administration (FDA) issued a second public health advisory in 2006 about a serious late adverse reaction to contrast agents known as Nephrogenic Systemic Fibrosis or Nephrogenic Fibrosing Dermopathy. Given the breadth of adverse events associated with intravascular delivery of contrast agents, improved medical devices are needed with coatings that do not inherently dose a patient with additional contrast agent in order to deliver a desired therapeutic agent.

Iodinated X-ray contrast agents are large hydrophilic spherical molecules. They are characterized by an extracellular distribution and rapid glomerular filtration and renal excretion. They are unable to cross membrane lipid bilayers to enter cells of the vasculature because they are large, polar, hydrophilic molecules. They are therefore not optimally effective at carrying hydrophobic drugs such as paclitaxel into cells, and the percent of paclitaxel reported to be taken up by vascular tissue after deployment of these devices is only 5-20%. In addition, the compatability or miscibility of paclitaxel and iopromide is not good, and the integrity and uniformity of the coating is poor. Particles from the coating easily flake off and are lost during handling. These deficiencies adversely affect the amount and uniformity of drug delivered to target tissue. Improved coatings are therefore needed, coatings that not only avoid unnecessary doses of contrast, but that also maintain integrity during handling and more effectively and uniformly deliver drug and facilitate its absorption by tissue.

Alternatively, balloon catheters are reported to have been coated with hydrophobic therapeutic agents that have been mixed with oils or lipids or encapsulated in particles such as liposomes or polymers. All of these drug delivery formulations have significant disadvantages. Unlike hydrophilic contrast agents, oils and lipids mix well with water-insoluble drugs such as paclitaxel or rapamycin, but the particle sizes of oils used for solubilizing the therapeutic agents are relatively unstable, ranging in a broad particle size distribution from several hundred nanometers to several microns in diameter.

Loading capacity of conventional micelles is low. Another disadvantage of oil-based liposome formulations is the dependence of drug absorption on the rate and extent of lipolysis. Lipolysis of oil-based triglycerides is difficult and dependent upon many factors, and triglycerides must be digested and drug released in order to be absorbed by diseased tissue. The amount of hydrophobic drug delivered to tissues by these agents will be low, because liposomes and micelles cannot efficiently release hydrophobic drug, which they carry away before it can be absorbed by tissues. Oils and lipids are therefore not effective at rapidly and efficiently facilitating tissue uptake of drug during a very brief device deployment time, and no report has shown these types of coatings to be effective. The ratio of drug to lipid in these formulations is typically 0.2-0.3, because the drugs are encapsulated in the particles, miscelles, or liposomes, which requires a significantly higher concentration of lipid than drug. These technologies involve forming the drug/lipid particles first and then coating medical devices with the prepared particles. There are several reports showing that drug release from these oil/lipid formulations occurs in the range of days to weeks or months. This property is not desirable for situations where drug release takes place in the range of seconds to minutes. Thus, the technology for oil/lipid formulation needs to be improved significantly in order to be useful in such situations.

Drug that is encapsulated in polymeric particles may take even longer to diffuse from the coating (the reported range is months to years) and will have further difficulty permeating target tissues rapidly. Microspheres formed with polymeric materials, such as polyesters, when used to encapsulate water insoluble drugs, are unable to release the drug until the polymeric material is degraded. Thus, these polymeric microspheres are useful for sustained release of drug over a long period of time, but cannot rapidly release drug and facilitate tissue uptake.

Combining drugs and medical devices is a complicated area of technology. It involves the usual formulation challenges, such as those of oral or injectable pharmaceuticals, together with the added challenge of maintaining drug adherence to the medical device until it reaches the target site and subsequently delivering the drug to the target tissues with the desired release and absorption kinetics. Drug coatings of medical devices must also have properties such that they do not crack upon expansion and contraction of the device, for example, of a balloon catheter or a stent. Furthermore, coatings must not impair functional performance such as burst pressure and compliance of balloons or the radial strength of self- or balloon-expanded stents. The coating thickness must also be kept to a minimum, since a thick coating would increase the medical device's profile and lead to poor trackability and deliverability. These coatings generally contain almost no liquid chemicals, which typically are often used to stabilize drugs. Thus, formulations that are effective with pills or injectables might not work at all with coatings of medical device. If the drug releases from the device too easily, it may be lost during device delivery before it can be deployed at the target site, or it may burst off the device during the initial phase of inflation and wash away before being pressed into contact with target tissue of a body lumen wall. If the drug adheres too strongly, the device may be withdrawn before the drug can be released and absorbed by tissues at the target tissues.

Thus, there is still a need to develop highly specialized coatings for medical devices that can rapidly deliver therapeutic agents, drugs, or bioactive materials directly into a localized tissue area during or following a medical procedure, so as to treat or prevent vascular and nonvascular diseases such as restenosis. The device should quickly release the therapeutic agent in an effective and efficient manner at the desired target location, where the therapeutic agent should rapidly permeate the target tissue to treat disease, for example, to relieve stenosis and prevent restenosis and late lumen loss of a body lumen.

SUMMARY OF THE INVENTION

The present inventor has found that coating the exterior surface of a medical device, and particularly of a balloon catheter or a stent, for example, with a layer comprising a therapeutic agent and an additive that has both a hydrophilic part and a drug affinity part is useful in solving the problems associated with the coatings discussed above. The drug affinity part is a hydrophobic part and/or has an affinity to the therapeutic agent by hydrogen bonding and/or van der Waals interactions. Surprisingly, the present inventor has found that the at least one additive according to embodiments of the present invention, which comprises a hydrophilic part and a drug affinity part, in combination with a therapeutic agent, forms an effective drug delivery coating on a medical device without the use of oils and lipids, thereby avoiding the lipolysis dependence and other disadvantages of conventional oil-based coating formulations. Moreover, the additives according to embodiments of the present invention facilitate rapid drug elution and superior permeation of drug into tissues at a disease site. Thus, coatings according to embodiments of the present invention provide an enhanced rate and/or extent of absorption of the hydrophobic therapeutic agent in diseased tissues of the vasculature or other body lumen. In embodiments of the present invention, the coated device delivers therapeutic agent to tissue during a very brief deployment time of less than 2 minutes and reduces stenosis and late lumen loss of a body lumen.

In one embodiment, the present invention relates to a medical device for delivering a therapeutic agent to a tissue, the device comprising a layer overlying an exterior surface of the medical device. The device includes one of a balloon catheter, a perfusion balloon catheter, an infusion catheter such as distal perforated drug infusion tube, a perforated balloon, spaced double balloon, porous balloon, and weeping balloon, a cutting balloon catheter, a scoring balloon catheter, a laser catheter, an atherectomy device, a debulking catheter, a stent, a filter, a stent graft, a covered stent, a patch, a wire, and a valve. Further, the tissue includes tissue of one of coronary vasculature, peripheral vasculature, cerebral vasculature, esophagus, airways, sinus, trachea, colon, biliary tract, urinary tract, prostate, and brain passages.

In one embodiment of the medical device, the coating layer overlying the surface of a medical device comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750.

In one embodiment, the coating layer overlying the exterior surface of the medical device comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is at least one of a surfactant and a chemical compound, and wherein the chemical compound has more than four hydroxyl groups. In one embodiment, the chemical compound having more than four hydroxyl groups has a melting point of 120° C. or less, and the chemical compound is an alcohol or an ester.

In one embodiment, the layer overlying the exterior surface of the medical device consists essentially of the therapeutic agent and the additive. In one embodiment, the layer overlying the exterior surface of the medical device does not include an iodine covalent bonded contrast agent. In one embodiment, the chemical compound has one or more hydroxyl, amino, carbonyl, carboxyl, acid, amide or ester groups. In one embodiment, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In another embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof.

In another embodiment, the coating layer overlying the surface of a medical device comprises a therapeutic agent and an additive, wherein the additive is a surfactant.

In another embodiment, the additive is a chemical compound having one or more hydroxyl, amino, carbonyl, carboxyl, acid, amide, ester groups. In another embodiment, the additive is a hydrophilic chemical compound with one or more hydroxyl, amino, carbonyl, carboxyl, acid, amide, or ester groups with a molecular weight of less than 5,000-10,000, preferably less than 1000-5,000, more preferably less than 750-1,000, or most preferably less than 750. Molecular weight of the additive is preferred to be less than that of the drug to be delivered. Small molecules can diffuse quickly, and they easily release from the surface of the delivery balloon, carrying drug with them. They quickly diffuse away from drug when the drug binds tissue. The molecular weight of the additives cannot be too low, however; additives with molecular weight less than 80 are not desirable because they evaporate easily and are not stable components of the coating. In another embodiment, the additive is a combination of a surfactant and a chemical compound with one or more hydroxyl, amino, carbonyl, carboxyl, acid, amide, or ester groups. In another embodiment, the additive is a combination of an amino alcohol and an organic acid; the combination is advantageous because it prevents instability that might otherwise arise due to reactivity of acids or amines with drugs such as paclitaxel. In another embodiment, the additive is hydroxyl ketone, hydroxyl lactone, hydroxyl acid, hydroxyl ester, or hydroxylamide. In another embodiment, the additive is gluconolactone or ribonic acid lactone thereof. In yet another embodiment, the additive is chosen from meglumine/lactic acid, meglumine/gentisic acid, meglumine/acetic acid, lactobionic acid, Tween 20/sorbitol, Tween 20/lactobionic acid, Tween 20/sugar or sugar derivatives and N-octanoyl N-methylglucamine. In another embodiment, the additive is a vitamin or derivative thereof. In another embodiment, the additive is an amino acid or derivative thereof. In another embodiment, the additive is a protein or derivative thereof. In another embodiment, the additive is an albumin. In another embodiment, the additive is soluble in an aqueous solvent and is soluble in an organic solvent. In another embodiment, the additive is an organic acid or an anhydride thereof. In yet another embodiment, the additive is chosen from sorbitan oleate and sorbitan fatty esters.

In another embodiment, the coating layer overlying the surface of a medical device comprises a therapeutic agent and an additive, wherein the additive is water-soluble, and wherein the additive is a chemical compound that has a molecular weight of from 80 to 750.

In one embodiment, the layer overlying the exterior surface of the medical device does not include oil, a lipid, or a polymer. In another embodiment, the layer overlying the exterior surface of the medical device does not include oil. In another embodiment, the layer overlying the exterior surface of the medical device does not include a polymer. In another embodiment, the layer overlying the exterior surface of the medical device does not include a purely hydrophobic additive. In one embodiment, the additive is not a therapeutic agent. In another embodiment, the additive is not salicylic acid or salts thereof.

In another embodiment, the coating layer overlying the surface of a medical device comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein the additive is chosen from p-isononylphenoxy-polyglycidol, PEG laurate, PEG oleate, PEG stearate, PEG glyceryl laurate, Tween 20, Tween 40, Tween 60, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerols, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol), and penta(propylene glycol), poly(propylene glycol) oligomers, and derivatives and combinations thereof.

In one embodiment, the therapeutic agent is one of paclitaxel and analogues thereof, rapamycin and analogues thereof, beta-lapachone and analogues thereof, biological vitamin D and analogues thereof, and a mixture of these therapeutic agents. In another embodiment, the therapeutic agent is in combination with a second therapeutic agent, wherein the therapeutic agent is one of paclitaxel, rapamycin, and analogues thereof, and wherein the second therapeutic agent is one of beta-lapachone, biological active vitamin D, and their analogues.

In one embodiment, the medical device comprising a layer overlying an exterior surface of the medical device further comprises an adherent layer between the exterior surface of the medical device and the layer. In another embodiment, the device further comprises a top layer overlying the surface of the layer to reduce loss of drug during transit through a body to the tissue. In another embodiment, the top layer overlying the surface of the layer overlying the exterior surface of the medical device comprises an additive that is less hydrophilic than the additive in the layer overlying the exterior surface of the medical device, and wherein the additive of the top layer is chosen from p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol, and penta(propylene glycol), poly(propylene glycol) oligomers, a block copolymer of polyethylene glycol and polypropylene glycol, and derivatives and combinations thereof.

In another embodiment, the medical device further comprises a dimethylsulfoxide solvent layer, wherein the dimethylsulfoxide solvent layer is overlying the surface of the layer.

In one embodiment of the medical device, the device is capable of releasing the therapeutic agent and the additive and delivering therapeutic agent to the tissue in about 0.1 to 2 minutes. In one embodiment, the concentration of the therapeutic agent in the layer is from 1 to 20 µg/mm$^2$. In one embodiment, the concentration of the therapeutic agent in the layer is from 2 to 10 µg/mm$^2$. In one embodiment, the therapeutic agent is not water-soluble.

In one embodiment, the additive enhances release of the therapeutic agent off the balloon. In another embodiment, the additive enhances penetration and absorption of the therapeutic agent in tissue. In another embodiment, the additive has a water and ethanol solubility of at least 1 mg/ml and the therapeutic agent is not water-soluble.

In another embodiment of the medical device, the layer overlying the exterior surface of the medical device comprises a therapeutic agent and at least two additives, wherein each of the additives comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein each additive is soluble in polar organic solvent and is soluble in water. In one aspect of this embodiment, the polar organic solvent is chosen from methanol, ethanol, isopropanol, acetone, dimethylformide, tetrahydrofuran, methylethyl ketone, dimethylsulfoxide, acetonitrile, ethyl acetate, and chloroform and mixtures of these polar organic solvents with water. In another aspect of this embodiment, the device further comprises a top layer overlying the surface of the layer overlying the exterior surface of the medical device to reduce loss of drug during transit through a body to the target tissue.

In another embodiment of the medical device, the layer overlying the exterior surface of the medical device comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive reduces crystal size and number of particles of the therapeutic agent, and wherein the additive is water-soluble and the therapeutic agent is not water-soluble.

In another embodiment of the medical device, the layer overlying the exterior surface of the medical device comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive has a fatty chain of an acid, ester, ether, or alcohol, wherein the fatty chain can directly insert into lipid membrane structures of the tissue, and wherein the therapeutic agent is not water-soluble.

In another embodiment of the medical device, the layer overlying the exterior surface of the medical device comprises a therapeutic agent and an additive, wherein the additive comprises a hydrophilic part and a hydrophobic part, wherein the additive can penetrate into and rearrange lipid membrane structures of the tissue, and wherein the therapeutic agent is not water-soluble and is not enclosed in micelles or encapsulated in polymer particles.

In another embodiment of the medical device, the layer overlying the exterior surface of the medical device comprises a therapeutic agent and an additive, wherein the additive comprises a hydrophilic part and a drug affinity part, wherein the additive has a fatty chain of an acid, ester, ether, or alcohol, wherein the fatty chain directly inserts into lipid membrane structures of tissue, wherein the additive has one or more functional groups which have affinity to the drug by hydrogen bonding and/or van der Waals interactions (the functional groups include hydroxyl, ester, amide, carboxylic acid, primary, second, and tertiary amine, carbonyl, anhydrides, oxides, and amino alcohols), wherein the therapeutic agent is not water-soluble and is not enclosed in micelles or encapsulated in polymer particles, and wherein the layer does not include a polymer, and the layer does not include an iodine covalent bonded contrast agent.

In yet another embodiment, the present invention relates to a stent coating for delivering a therapeutic agent to a tissue, the stent coating comprising a layer overlying a surface of the stent. In one aspect of this embodiment, the layer overlying the surface of the stent comprises a therapeutic agent, an additive, and a polymer matrix, wherein the therapeutic agent is dispersed, but not encapsulated, as particles in the polymer matrix, wherein the additive comprises a hydrophilic part and a drug affinity part, wherein the drug affinity is at least one of a hydrophobic part, a part that has an affinity to the therapeutic agent by hydrogen bonding, and a part that has an affinity to the therapeutic agent by van der Waals interactions. In one aspect of this embodiment, the additive improves the compatibility of the therapeutic agent and the polymer matrix, the additive reduces the particle sizes and improves uniformity of distribution of the therapeutic agent in the polymer matrix, and the additive enhances rapid release of drug from the polymer matrix.

In yet another embodiment, the present invention relates to a medical device coating for delivering a drug to a tissue that is prepared from a mixture. In one aspect of this embodiment, the coating is prepared from a mixture comprising an organic phase containing drug particles dispersed therein and an aqueous phase containing a water-soluble additive. In one aspect of this embodiment, the water-soluble additive is chosen from polyethylene glycol, polyvinyl alcohol, polyvinylpyrrolidinone, polypeptides, water-soluble surfactants, water-soluble vitamins, and proteins. In another aspect of this embodiment, the preparation of the mixture includes homogenization under high shear conditions and optionally under pressure.

In another embodiment, the present invention relates to a balloon catheter for delivering a therapeutic agent to a blood vessel, the catheter comprising a coating layer overlying an exterior surface of a balloon. In one embodiment of the balloon catheter, the coating layer comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, and wherein the additive is at least one of a surfactant and a chemical compound, and wherein the chemical compound has a molecular weight of from 80 to 750.

In another embodiment of the balloon catheter, the coating layer comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is at least one of a surfactant and a chemical compound, and wherein the chemical compound has more than four hydroxyl groups. In one aspect of this embodiment, the chemical compound having more than four hydroxyl groups has a melting point of 120° C. or less, and the chemical compound is an alcohol or an ester.

In one embodiment of the balloon catheter, the coating layer overlying an exterior surface of the exterior surface of the medical device consists essentially of the therapeutic agent and the additive. In another embodiment, the layer overlying the exterior surface of the medical device does not include an iodine covalent bonded contrast agent.

In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof. In one embodiment, the chemical compound has one or more hydroxyl, amino, carbonyl, carboxyl, acid, amide or ester groups. In one embodiment, the chemical compound having one or more hydroxyl, amino, carbonyl, carboxyl, acid, amide or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In one embodiment of the balloon catheter, the coating layer overlying the exterior surface of the balloon does not include a purely hydrophobic additive. In another embodiment, the coating layer overlying the surface of the balloon does not contain an iodinated contrast agent. In another embodiment, the additive is not a therapeutic agent. In another embodiment, the additive is not salicylic acid or salts thereof. In another embodiment, the coating layer overlying the surface of the balloon does not include oil, a lipid, or a polymer. In yet another embodiment, the coating layer overlying the surface of the balloon does not include oil. In another aspect of this embodiment, the coating layer does not include a polymer.

In one embodiment of the balloon catheter, the additive in the coating layer comprising the therapeutic agent and the additive is chosen from p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol), and penta(propylene glycol), poly(propylene glycol) oligomers, a block copolymer of polyethylene glycol and polypropylene glycol, and derivatives and combinations thereof.

In one embodiment, the therapeutic agent is one of paclitaxel and analogues thereof, rapamycin and analogues thereof, beta-lapachone and analogues thereof, biological vitamin D and analogues thereof, and a mixture of these therapeutic agents. In another embodiment, the therapeutic agent is in combination with a second therapeutic agent, wherein the therapeutic agent is one of paclitaxel, rapamycin, and analogues thereof, and wherein the second therapeutic agent is one of beta-lapachone, biological active vitamin D, and their analogues. In one embodiment, the therapeutic agent is not water soluble.

In one embodiment, the additive is soluble in an organic solvent and in water. In another embodiment, the additive enhances penetration and absorption of the therapeutic agent in tissue of the blood vessel. In another embodiment, the therapeutic agent is not water-soluble. In another embodiment, the additive has water and ethanol solubility of at least 1 mg/ml, and the therapeutic agent is not water-soluble.

In one embodiment of the balloon catheter, the catheter further comprises an adherent layer between the exterior surface of the balloon and the coating layer. In another embodiment, the catheter further comprises a top layer overlying the coating layer, wherein the top layer reduces loss of the therapeutic agent during transit through a body to the blood vessel. The top layer comprises an additive selected from those additives, according to embodiments of the invention described herein. The top layer will be slowly dissolved during transit through a body to the body lumen to the target site for therapeutic intervention. This top layer will reduce drug loss during transit and increase the drug available to the tissue when the medical device of embodiments of the present invention is pressed into contact with luminal tissue. In one embodiment, the additive in the top layer is less hydrophilic than the additive in the coating layer. In another embodiment, the catheter further comprises a dimethylsulfoxide solvent layer, wherein the dimethylsulfoxide solvent layer is overlying the surface of the coating layer.

In one embodiment, the balloon catheter is capable of releasing the therapeutic agent and the additive and delivering the therapeutic agent to the blood vessel in about 0.1 to 2 minutes.

In one embodiment of the balloon catheter, the concentration of the therapeutic agent in the coating layer is from 1 to 20 µg/mm$^2$. In another embodiment, the concentration of the therapeutic agent in the coating layer is from 2 to 10 µg/mm$^2$.

In yet a further embodiment, the present invention relates to a balloon catheter for delivering a therapeutic agent to a blood vessel. In one aspect of this embodiment, the catheter comprises an elongate member having a lumen and a distal end, an expandable balloon attached to the distal end of the elongate member and in fluid communication with the lumen, and a coating layer overlying an exterior surface of the balloon. In one aspect of this embodiment, the coating layer overlying the surface of the balloon comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750, and wherein the catheter is capable of releasing the therapeutic agent and the additive and delivering the therapeutic agent to tissue of the blood vessel in less than about 2 minutes. In one aspect of this embodiment, the layer does not contain an iodinated contrast agent.

In one embodiment, the balloon catheter further comprises a dimethylsulfoxide solvent layer overlying the coating layer, wherein the dimethylsulfoxide layer enhances the ability of the therapeutic agent to penetrate into the blood vessel. In another embodiment, the balloon catheter further comprises an adherent layer between the exterior surface of the balloon and the coating layer. In yet another embodiment, the balloon catheter further comprises a top layer overlying the coating layer, wherein the top layer maintains integrity of the coating layer during transit through a blood vessel to the target site for therapeutic intervention.

In one embodiment, the concentration of the therapeutic agent in the coating layer is from 2.5 to 6 µg/mm$^2$. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof. In one embodiment, the chemical compound has one or more hydroxyl, amino, carbonyl, carboxyl, acid, amide or ester groups. In one embodiment, the chemical compound having one or more hydroxyl, amino, carbonyl, carboxyl, acid, amide or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the chemical compound has more than four hydroxyl groups and has a melting point of 120° C. or less, and the chemical compound is an alcohol or an ester.

In one embodiment of the balloon catheter, the additive is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, Tween 20, Tween 40, Tween 60, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

In yet a further embodiment, the present invention relates to a pharmaceutical composition comprising a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750. In one aspect of this embodiment, the pharmaceutical composition does not include an iodine covalent bonded contrast agent or a polymer, and wherein the therapeutic agent is not encapsulated in miscelles or particles.

In one embodiment, the chemical compound has one or more hydroxyl, amino, carbonyl, carboxyl, acid, amide or ester groups. In one embodiment, the chemical compound having one or more hydroxyl, amino, carbonyl, carboxyl, acid, amide or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the chemical compound has more than four hydroxyl groups and has a melting point of 120° C. or less, and the chemical compound is an alcohol or an ester. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof.

In one embodiment of the pharmaceutical composition, the additive is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, Tween 20, Tween 40, Tween 60, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

In yet a further embodiment, the present invention relates to a method for treating a diseased body lumen or cavity after a surgical or interventional procedure comprising delivering a pharmaceutical composition at a surgical site by injection or spraying with a catheter, wherein the composition comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is at least one of a surfactant and a chemical compound, and wherein the chemical compound has a molecular weight of from 80 to 750. In one embodiment, the chemical compound has one or more hydroxyl, amino, carbonyl, carboxyl, acid, amide or ester groups. In one embodiment, the additive is water-soluble, and wherein the composition does not include an iodine covalent bonded contrast agent.

In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof. In one embodiment, the chemical compound having one or more hydroxyl, amino, carbonyl, carboxyl, acid, amide or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In yet a further embodiment, the present invention relates to a pharmaceutical composition for treating a cancer including cancers of the ovary, breast, lung, esophagus, head and neck region, bladder, prostate, brain, liver, colon and lymphomas, wherein the composition comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the therapeutic agent is not enclosed in micelles or encapsulated in polymer particles, and wherein the composition does not include an iodine covalent bonded contrast agent. In one aspect of this embodiment, the therapeutic agent is chosen from paclitaxel and analogues thereof and rapamycin and analogues thereof.

In yet a further embodiment, the present invention relates to a solution for coating a medical device. In one aspect of this embodiment, the solution comprises an organic solvent, a therapeutic agent, and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750. In another embodiment, the solution for coating a medical device does not include an iodine covalent bonded contrast agent, an oil, a lipid, or a polymer.

In one embodiment, the chemical compound has one or more hydroxyl, amino, carbonyl, carboxyl, acid, amide or ester groups. In one embodiment, the chemical compound having one or more hydroxyl, amino, carbonyl, carboxyl, acid, amide or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof. In one embodiment, the therapeutic agent is paclitaxel or rapamycin or analog or derivative thereof.

In another embodiment, the additive in the coating solution is chosen from wherein the additive is chosen from p-isononylphenoxypolyglycidol, PEG laurate, PEG oleate, PEG stearate, PEG glyceryl laurate, Tween 20, tween 60, Tween 80, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfosuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol), and penta(propylene glycol), poly(propylene glycol) oligomers, a block copolymer of polyethylene glycol and polypropylene glycol, and derivatives and combinations thereof.

In yet a further embodiment, the present invention relates to a medical device for delivering a therapeutic agent to a tissue, the device comprising a first layer applied to an exterior surface of the medical device, and a second layer overlying the first layer. In one aspect of this embodiment, the first layer comprises a therapeutic agent, and the second layer comprises an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. In one aspect of this embodiment, the first layer further comprises an additive, wherein the additive is water-soluble and the layer does not include an iodinated contrast agent. In another aspect of this embodiment, the second layer further comprises a therapeutic agent. In yet a further aspect of this embodiment, the first layer further comprises an additive and the second layer further comprises a therapeutic agent.

In a further embodiment, the present invention relates to a two layer coating comprising a first layer comprising a therapeutic agent, and a top layer comprising an additive. In one aspect of this embodiment, the top layer may be overlying the first layer. In one aspect of this embodiment, the additive in both the first layer and in the top layer comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750. In one aspect of this embodiment, the first layer does not include an iodine covalent bonded contrast agent. In another aspect of this embodiment, the top layer further comprises a therapeutic agent.

In a further embodiment, the present invention relates to a method for preparing a medical device. In one aspect of this embodiment, the method comprises (a) preparing a coating solution comprising an organic solvent, a therapeutic agent, and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750, (b) applying the coating solution to a medical device, and (c) drying the coating solution, forming a coating layer. In one aspect of this embodiment, the coating layer does not include an iodine covalent bonded contrast agent. In one aspect of this embodiment, the coating solution is applied by dipping a portion of the exterior surface of the medical device in the coating solution. In another aspect of this embodiment, the coating solution is applied by spraying a portion of the exterior surface of the medical device with a coating solution. In another aspect of this embodiment, steps (b) and (c) are repeated until a therapeutically effective amount of the therapeutic agent in the coating layer is deposited on the surface of the medical device. In another aspect of this embodiment, the total thickness of the coating layer is from about 0.1 to 200 microns. In yet another aspect of this embodiment, the method further comprises applying a dimethylsulfoxide solvent to the dried coating layer obtained in step (c).

In a further embodiment, the present invention relates to a method for preparing a drug coated balloon catheter. In one aspect of this embodiment, the method comprises, (a) preparing a coating solution comprising an organic solvent, a therapeutic agent, and an additive, wherein the additive comprises a hydrophilic part and a drug affinity part, wherein the drug affinity is at least one of a hydrophobic part, a part that has an affinity to the therapeutic agent by hydrogen bonding, and a part that has an affinity to the therapeutic agent by van der Waals interactions, wherein the additive is at least one of a surfactant and a chemical compound, and wherein the chemical compound has a molecular weight of from 80 to 750, (b) applying the coating solution to an inflated balloon catheter, and (c) deflating and folding the balloon catheter and drying the coating solution to increase uniformity of drug coating.

In a further embodiment, the present invention relates to a method for treating a blood vessel. In one aspect of this embodiment, the method comprises inserting a medical device comprising a coating layer into the blood vessel, wherein the coating layer comprises a therapeutic agent and an additive, wherein the additive comprises a hydrophilic part and a drug affinity part, wherein the drug affinity is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750, and releasing the therapeutic agent and the additive and delivering the therapeutic agent into the tissue of the blood vessel in 2 minutes or less. In one aspect of this embodiment, the coating layer does not include an iodine covalent bonded contrast agent.

In a further embodiment, the present invention relates to a method for treating a total occlusion or narrowing of body passages. In one aspect of this embodiment, the method comprises removing plaques from the body passage, inserting a medical device comprising a coating layer into the body passage, wherein the coating layer comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is at least one of a surfactant and a chemical compound, and wherein the chemical compound has a molecular weight of from 80 to 750, and releasing the therapeutic agent and the additive and delivering the therapeutic agent into the tissue of the body passage in 2 minutes or less.

In a further embodiment, the present invention relates to a method for treating tissue of a body comprising bringing a medical device comprising a coating layer into contact with tissue of the body, wherein the coating layer comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750, and releasing the therapeutic agent and the additive and delivering the therapeutic agent into the tissue in 2 minutes or less. In one embodiment, the coating layer does not include an iodine covalent contrast agent. In one aspect of this embodiment, the tissue includes tissue of one of coronary vasculature, peripheral vasculature, cerebral vasculature, esophagus, airways, sinus, trachea, colon, biliary tract, urinary tract, prostate, and brain passages.

In yet a further embodiment, the present invention relates to a process of producing a balloon catheter. In one aspect of this embodiment, the process comprises preparing a solution comprising an organic solvent, a therapeutic agent, and an additive, wherein the additive comprises a hydrophilic part and a drug affinity part, wherein the drug affinity is at least one of a hydrophobic part, a part that has an affinity to the therapeutic agent by hydrogen bonding, and a part that has an affinity to the therapeutic agent by van der Waals interactions, wherein the additive is water-soluble, wherein the additive is at least one of a surfactant and a chemical compound, and wherein the chemical compound has a molecular weight of from 80 to 750, applying the solution to the balloon catheter, and evaporating the solvent. In one embodiment, the solution does not contain an iodinated contrast agent.

In yet a further embodiment, the present invention relates to a medical device comprising a layer overlying an exterior surface of the medical device, the layer comprising a therapeutic agent and an additive, wherein the additive is one of PEG fatty ester, PEG fatty ether, and PEG fatty alcohols. In one aspect of this embodiment, the additive is chosen from wherein the additive is chosen from PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, PEG-20 oleate, PEG-20 dilaurate, PEG-20 dioleate, PEG-20 distearate, PEG-32 dilaurate and PEG-32 dioleate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is one of glycerol and polyglycerol fatty esters and PEG glycerol fatty esters. In one aspect of this embodiment, the additive is chosen from polyglyceryl oleate, polyglyceryl-2 dioleate, polyglyceryl-10 trioleate, polyglyceryl stearate, polyglyceryl laurate, polyglyceryl myristate, polyglyceryl palmitate, polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, polyglyceryl polyricinoleates, PEG-20 glyceryl laurate, PEG-30 glyceryl laurate, PEG-40 glyceryl laurate, PEG-20 glyceryl oleate, and PEG-30 glyceryl oleate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, a cutting balloon catheter, a scoring balloon catheter, a laser catheter, an atherectomy device, a debul king catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is one of sorbitan fatty esters, and PEG sorbitan esters. In one aspect of this embodiment, the additive is chosen from sorbitan monolaurate, sorbitan monopalmitate, sorbitan monooleate, sorbitan monostearate, PEG-20 sorbitan monolaurate, PEG-20 sorbitan monopalmitate, PEG-20 sorbitan monooleate, and PEG-20 sorbitan monostearate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is a chemical compound containing a phenol moiety. In one aspect of this embodiment, the additive is chosen from p-isononylphenoxypolyglycidol, octoxynol, monoxynol, tyloxapol, octoxynol-9, and monoxynol-9. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, the additive is chosen from sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside, D-glucoascorbic acid and its salt, tromethamine, glucamine, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, and glucosamine. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, a cutting balloon catheter, a scoring balloon catheter, a laser catheter, an atherectomy device, a debul king catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is an ionic surfactant. In one aspect of this embodiment, the additive is chosen from benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, and sodium taurocholate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, infusion catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is a vitamin or vitamin derivative. In one aspect of this embodiment, the additive is chosen from acetiamine, benfotiamine, pantothenic acid, cetotiamine, cyclothiamine, dexpanthenol, niacinamide, nicotinic acid and its salts, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, vitamin U, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K-S(II). In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, infusion catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent and an additive, wherein the additive is an amino acid, an amino acid salt, or an amino acid derivative. In one aspect of this embodiment, the additive is chosen from alanine, arginine, asparagine, aspartic acid, cysteine, glutamic acid, glutamine, glycine, histidine, proline, isoleucine, leucine, lysine, methionine, phenylalanine, serine, threonine, tryptophan, tyrosine, valine, and derivatives thereof. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, infusion catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device for delivering a therapeutic agent to a tissue, the device comprising a layer overlying an exterior surface of the medical device, the layer comprising a therapeutic agent and an additive, wherein the additive is a peptide, oligopeptide, or protein. In one aspect of this embodiment, the additive is chosen from albumins, immunoglobulins, caseins, hemoglobins, lysozymes, immunoglobins, a-2-macroglobulin, fibronectins, vitronectins, firbinogens, and lipases. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, infusion catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device for delivering a therapeutic agent to a tissue, the device comprising a layer overlying an exterior surface of the medical device, the layer comprising a therapeutic agent and an additive, wherein the additive includes a combination or mixture of both a surfactant and a chemical compound, wherein the chemical compound has one or more hydroxyl, amino, carbonyl, carboxyl, acid, amide or ester groups. In one aspect of this embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof. In another aspect of this embodiment, the chemical compound having one or more hydroxyl, amino, carbonyl, carboxyl, acid, amide or ester groups has a molecular weight of from 80 to 750. In another aspect of this embodiment, the chemical compound is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, sorbitan, glycerol, polyalcohol, phosphates, sulfates, organic acids, esters, salts, vitamins, combinations of amino alcohol and organic acid, and their substituted molecules. In another aspect of this embodiment, the chemical compound having one or more hydroxyl, amino, carbonyl, carboxyl, acid, amide or ester groups is chosen from acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic acid and anhydride, glutaric acid and anhydride, ascorbic acid, citric acid, tartaric acid, lactic acid, oxalic acid aspartic acid, nicotinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, infusion catheter, a cutting balloon catheter, a scoring balloon catheter, a laser catheter, an atherectomy device, a debulking catheter, a stent, a filter, a stent graft, a covered stent, a patch, a wire, and a valve.

In another embodiment, the present invention relates to a pharmaceutical formulation for administration to a mammal comprising paclitaxel or rapamycin or derivatives thereof; and a combination of both a surfactant and a chemical compound, wherein the chemical compound has one or more hydroxyl, amino, carbonyl, carboxyl, acid, amide or ester groups. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof. In one embodiment, the chemical compound having one or more hydroxyl, amino, carbonyl, carboxyl, acid, amide or ester groups has a molecular weight of from 80 to 750. In one embodiment, the chemical compound having one or more hydroxyl, amino, carbonyl, carboxyl, acid, amide, or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sugars, glucose, sucrose, sorbitan, glycerol, polyalcohol, phosphates, sulfates, organic acids, esters, salts, vitamins, combinations of amino alcohol and organic acid, and their substituted molecules. In one embodiment, the chemical compound having one or more hydroxyl, amino, carbonyl, carboxyl, acid, amide or ester groups is chosen from L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, acetaminophen, ibuprofen, retinoic acid, lysine acetate, gentisic acid, catechin, catechin gallate, tiletamine, ketamine, propofol, lactic acids, acetic acid, ribonic acid lactone, meglumine/lactic acid, meglumine/gentisic acid, meglumine/acetic acid, sorbitol, xylitol, 2-ethoxyethanol, sugars, galactose, glucose, mannose, xylose, sucrose, lactose, maltose, cyclodextrin, (2-hydroxypropyl)-cyclodextrin, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

In another embodiment, the present invention relates to a pharmaceutical formulation for administration to a mammal comprising paclitaxel or rapamycin or derivatives thereof, and a chemical compound with one or more hydroxyl, amino, carbonyl, carboxyl, acid, amide or ester groups, wherein the chemical compound with one or more hydroxyl, amino, carbonyl, carboxyl, acid, amide or ester groups has a molecular weight of from 80 to 750. In one embodiment, the chemical compound with one or more hydroxyl, amino, carbonyl, carboxyl, acid, amide, or ester groups is chosen from hydroxyl ketone, hydroxyl lactone, gluconolactone, glucoheptonolactone, glucooctanoic lactone, gulonic acid lactone, mannoic lactone, ribonic acid lactone, sugar phosphate, sugar sulfate, catechin, catechin gallate, and combinations of amino alcohol and organic acid. In one aspect of this embodiment, the amino alcohol is chosen from tromethamine, triethanolamine, diethanolamine, meglumine, glucamine, glucosamine, lysine, and derivatives thereof; and the organic acid is chosen from glucoheptonic acid, glucomic acid, glutamic acid, benzoic acid, hydroxybenzoic acid, gentisic acid, lactobionic acid, vanillic acid, lactic acids, acetic acid, and derivatives thereof.

In yet another embodiment, the present invention relates to a pharmaceutical formulation for administration to a mammal comprising: paclitaxel or rapamycin or derivatives thereof; and a combination of amino alcohol and organic acid, wherein the amino alcohol is chosen from tromethamine, triethanolamine, diethanolamine, meglumine, glucamine, glucosamine, lysine, and derivatives thereof; and the organic acid is chosen from glucoheptonic acid, glucomic acid, glutamic acid, benzoic acid, hydroxybenzoic acid, gentisic acid, lactobionic acid, vanillic acid, lactic acids, acetic acid, and derivatives thereof.

In yet another embodiment, the present invention relates to a medical device for delivering a therapeutic agent to a tissue, the device comprising a layer overlying an exterior surface of the medical device, the layer comprising a therapeutic agent and an additive, wherein the additive is chosen from hydroxyl ketone, hydroxyl lactone, gluconolactone, glucoheptonolactone, glucooctanoic lactone, gulonic acid lactone, mannoic lactone, ribonic acid lactone and lactobionic acid.

In yet another embodiment, the present invention relates to a medical device for delivering a therapeutic agent to a tissue, the device comprising a layer overlying an exterior surface of the medical device, the layer comprising a therapeutic agent and an additive, wherein the therapeutic agent is paclitaxel and analogues thereof or rapamycin and analogues thereof, and the additive is chosen from sorbitol, diethylene glycol, triethylene glycol, tetraethylene glycol, polyethylene glycol oligomers, polypropylene glycol oligomers, block copolymer oligomers of polyethylene glycol and polypropylene glycol, xylitol, 2-ethoxyethanol, sugars, galactose, glucose, mannose, xylose, sucrose, lactose, maltose, Tween 20, Tween 40, Tween 60, and their derivatives, wherein the ratio by weight of drug to additive is from 0.5 to 3, wherein the therapeutic agent and the additive are simultaneously released.

Many embodiments of the present invention are particularly useful for treating vascular disease and for reducing stenosis and late luminal loss, or are useful in the manufacture of devices for that purpose.

It is understood that both the foregoing general description and the following detailed description are exemplary and explanatory only and are not restrictive of the present invention as claimed.

DETAILED DESCRIPTION OF EXEMPLARY EMBODIMENTS

Embodiments of the present invention relate to medical devices, including particularly balloon catheters and stents, having a rapid drug-releasing coating and methods for preparing such coated devices. The therapeutic agent according to embodiments of the present invention does not require a delayed or long term release and instead preferably the therapeutic agent and the additive are released in a very short time period to provide a therapeutic effect upon contact with tissue. An object of embodiments of the present invention is to facilitate rapid and efficient uptake of drug by target tissue during transitory device deployment at a target site.

Figure 1:
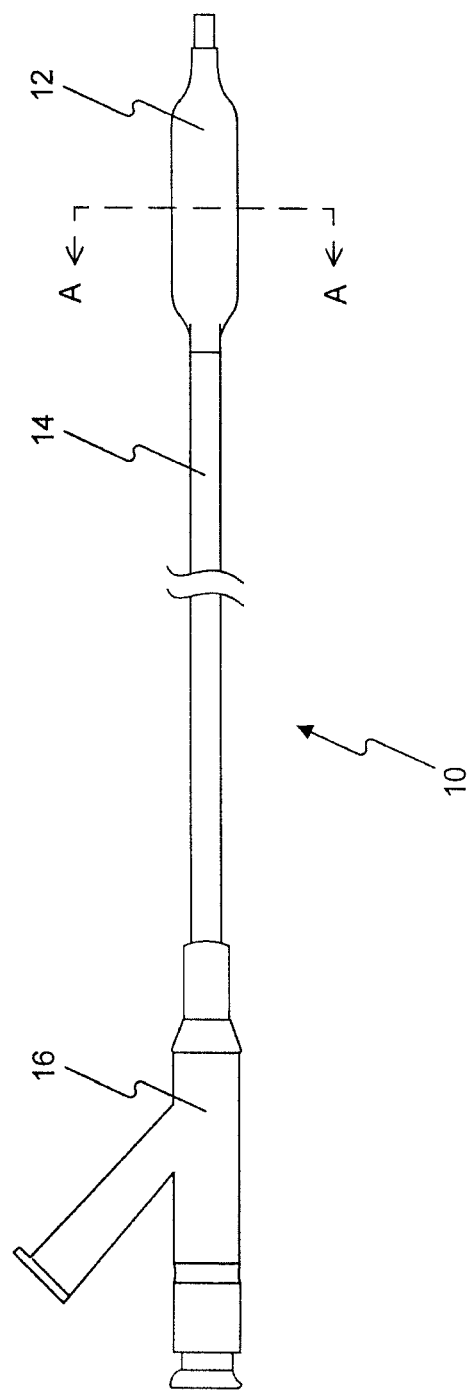
FIG. 1 is a perspective view of an exemplary embodiment of a balloon catheter according to the present invention.

As shown in FIG. 1, in one embodiment, the medical device is a balloon catheter. The balloon catheter may be any suitable catheter for the desired use, including conventional balloon catheters known to one of ordinary skill in the art. For example, balloon catheter 10 may include an expandable, inflatable balloon 12 at a distal end of the catheter 10, a handle assembly 16 at a proximal end of the catheter 10, and an elongate flexible member 14 extending between the proximal and distal ends. Handle assembly 16 may connect to and/or receive one or more suitable medical devices, such as a source of inflation media (e.g., air, saline, or contrast media). Flexible member 14 may be a tube made of suitable biocompatible material and having one or more lumens therein. At least one of the lumens is configured to receive inflation media and pass such media to balloon 12 for its expansion. The balloon catheter may be a rapid exchange or over-the-wire catheter and made of any suitable biocompatible material.

Figure 2A:
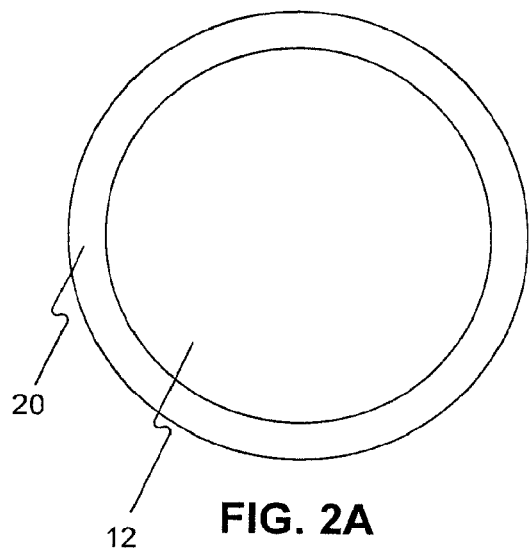
FIGS. 2A-2C are cross-sectional views of different embodiments of the distal portion of the balloon catheter of FIG. 1, taken along line A-A, showing exemplary coating layers.
Figure 2B:
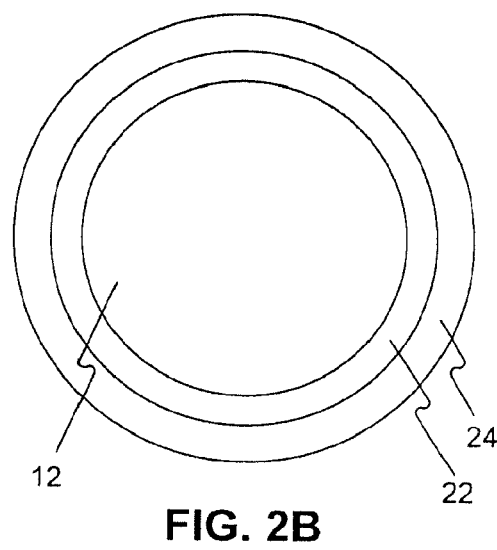

In one embodiment, the present invention provides a medical device for delivering a therapeutic agent to a tissue. The device includes a layer applied to an exterior surface of the medical device, such as a balloon catheter or stent, for example. The layer includes a therapeutic agent and an additive. For example, as shown in the embodiment depicted in FIG. 2A, the balloon 12 is coated with a layer 20 that includes a therapeutic agent and an additive. In some embodiments, the layer consists essentially of a therapeutic agent and an additive, i.e., the layer includes only the therapeutic agent and the additive, without any other materially significant components. In some embodiments, the device may optionally include an adherent layer. For example, as shown in the embodiment depicted in FIG. 2B, the balloon 12 is coated with an adherent layer 22. A layer 24 that includes a therapeutic agent and an additive is overlying the adherent layer. The adherent layer, which is a separate layer underlying the drug coating layer, improves the adherence of the drug coating layer to the exterior surface of the medical device and protects coating integrity. For example, if drug and additive differ in their adherence to the medical device, the adherent layer may prevent differential loss of components and maintain drug-to-additive ratio in the coating during transit to a target site for therapeutic intervention. Furthermore, the adherent layer may function to facilitate rapid release of coating layer components off the device surface upon contact with tissues at the target site. In other embodiments, the device may include a top layer. The top layer may reduce loss of the drug layer before it is brought into contact with target tissues, for example during transit of the balloon 12 to the site of therapeutic intervention or during the first moments of inflation of balloon 12 before coating layer 20 is pressed into direct contact with target tissue.

In one embodiment, the concentration density of the at least one therapeutic agent applied to the surface of the medical device is from about 1 to 20 μg/mm$^2$, or more preferably from about 2 to 6 μg/mm$^2$. The ratio by weight of therapeutic agent to the additive is from about 0.5 to 100, for example, from about 0.1 to 5, from 0.5 to 3, and further for example, from about 0.8 to 1.2. If the ratio (by weight) of the therapeutic agent to the additive is too low, then drug may release prematurely, and if the ratio is too high, then drug may not elute quickly enough or be absorbed by tissue when deployed at the target site.

In another embodiment, the layer comprises a therapeutic agent and an additive, wherein the therapeutic agent is paclitaxel and analogues thereof or rapamycin and analogues thereof, and the additive is chosen from sorbitol, diethylene glycol, triethylene glycol, tetraethylene glycol, xylitol, 2-ethoxyethanol, sugars, galactose, glucose, mannose, xylose, sucrose, lactose, maltose, Tween 20, Tween 40, Tween 60, and their derivatives, wherein the ratio by weight of the therapeutic agent to the additive is from 0.5 to 3. If the ratio of drug to additive is below 0.5, then drug may release prematurely, and if ratio is above 3, then drug may not elute quickly enough or be absorbed by tissue when deployed at the target site. In other embodiments, the layer may include a therapeutic agent and more than one additive. For example, one additive may serve to improve balloon adhesion of another additive or additives that are superior at promoting drug release or tissue uptake of drug.

In other embodiments, the layer may include at least one therapeutic agent, at least one additive, and at least one polymer carrier for coating of a medical device such as a stent or a balloon. The therapeutic agent is not encapsulated in polymer particles. The additive in the layer improves compatibility of the drug and polymer carrier. It reduces the size or eliminates drug crystal particles in the polymer matrix of the coating. The uniform drug distribution in the coating improves clinical outcomes by more uniformly delivering drug to target tissues.

In another embodiment, the device comprises two layers applied to an exterior surface of the medical device, and particularly a balloon catheter, for example. The first layer comprises a therapeutic agent. The first layer may optionally comprise an additive or additives. The second layer comprises an additive or additives. The second layer may optionally include at least a therapeutic agent. When the first and second layers both contain a therapeutic agent, the content of the therapeutic agent in the second layer is lower than the content of the therapeutic agent in the first layer. In one embodiment, the second layer is overlying the first layer. In this arrangement, the second layer can prevent drug loss during deployment of the medical device into body passageways, for example, as a balloon catheter traverses the tortuous anatomy to a tissue site in the vasculature.

In another embodiment, the device comprises two layers applied to an exterior surface of the medical device, and particularly a balloon catheter, for example. The first layer comprises a therapeutic agent. The first layer may optionally comprise an additive or additives. The second layer comprises an additive or additives. The second layer may optionally include at least a therapeutic agent. When the first and second layers both contain a therapeutic agent, the content of the therapeutic agent in the first layer is lower than the content of the therapeutic agent in the second layer. In one embodiment, the second layer is overlying the first layer. This arrangement is useful, for example, in the case of a therapeutic agent that adheres too tightly to the balloon surface to rapidly elute off the balloon when inflated at the target site. In this arrangement, the first layer functions to facilitate rapid release of the bulk of drug, which is in the second layer, off the surface of the device while it is inflated at the target site of therapeutic intervention.

In other embodiments, two or more therapeutic agents are used in combination in the drug-additive layer.

Figure 2C:
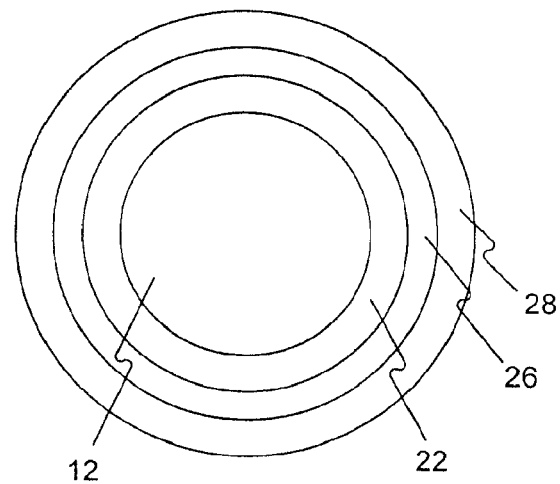

In a further embodiment, the device having a two layer coating may optionally include an adherent layer. The adherent layer does not contain a therapeutic agent. For example, as shown in the embodiment depicted in FIG. 2C, the balloon 12 is coated with an adherent layer 22. A first layer 26 that comprises a therapeutic agent and optionally an additive or additives is overlying the adherent layer 22. A second layer 28 that comprises an additive and optionally a therapeutic agent is overlying the first layer 26. The adherent layer improves the adherence of the first layer to the exterior surface of the medical device and protects the integrity of the first layer. For example, if drug and additive or additives in the first layer differ in their strength of adherence to the medical device, the adherent layer may prevent differential loss of components and maintain drug-to-additive and additive-to-additive ratio in the first and second layers during transit to a target site for therapeutic intervention. Furthermore, the adherent layer may function to facilitate rapid elution of coating layer off the device surface upon contact with tissues at the target site. In one embodiment, the first layer, the second layer, and the adherent layer each contain an additive.

Optionally, post-treatment with dimethylsulfoxide (DMSO) or other solvent may be advantageous since DMSO may further enhance penetration and absorption of drug into tissue. DMSO displaces water from the lipid head groups and protein domains of the membrane lipid bilayer of target cells to indirectly loosen the lipid structure, accelerating drug absorption and penetration.

In a further embodiment, the present invention relates to a pharmaceutical composition for treating a diseased body lumen or cavities after surgical or interventional procedures (PTCA, PTA, stent placement, excision of diseased tissue such as cancer, and relieving or treating stenosis), wherein the pharmaceutical composition comprises a therapeutic agent and an additive, wherein the additive comprises a hydrophilic part and a drug affinity part, wherein the drug affinity part is a hydrophobic part and/or has an affinity to the therapeutic agent by hydrogen bonding and/or van der Waals interactions, and wherein the therapeutic agent is not enclosed in micelles or encapsulated in polymer particles.

In another embodiment, a method of preventing complications or recurrence of disease (such as cancer or restenosis) after a surgical or interventional procedure such as PTCA, PTA, stent deployment, stenosis or plaque removal by debulking, atherectomy, or laser procedures, the pharmaceutical composition is locally delivered at or near the site of intervention by means of a coated medical device (such as a drug-coated balloon), or by spray, by injection, or by deposition. For example, the pharmaceutical composition may be delivered by spray, injection, balloon or other method of deposition, into cavities created by surgical removal of cancer tissue in order to reduce the risk of recurrence. As another example, a method for delivering the pharmaceutical composition comprises inserting a medical device (such as guide catheter or a drug infusion catheter) into the blood to inject the pharmaceutical composition after a vascular intervention such as PTCA, PTA, or stent placement to prevent restenosis, wherein the pharmaceutical composition comprises a therapeutic agent and an additive, wherein the additive comprises a hydrophilic part and a drug affinity part, wherein the drug affinity part is a hydrophobic part and/or has an affinity to the therapeutic agent by hydrogen bonding and/or Van der Waals interactions, and wherein the therapeutic agent is not enclosed in micelles or encapsulated in polymer particles.

Many embodiments of the present invention are particularly useful for treating vascular disease and for reducing stenosis and late luminal loss, or are useful in the manufacture of devices for that purpose or in methods of treating that disease.

Additive

The additive of embodiments of the present invention has two parts. One part is hydrophilic and the other part is a drug affinity part. The drug affinity part is a hydrophobic part and/or has an affinity to the therapeutic agent by hydrogen bonding and/or van der Waals interactions. The drug affinity part of the additive may bind the lipophilic drug, such as rapamycin or paclitaxel. The hydrophilic portion accelerates diffusion and increases permeation of the drug into tissue. It may facilitate rapid movement of drug off the medical device during deployment at the target site by preventing hydrophobic drug molecules from clumping to each other and to the device, increasing drug solubility in interstitial spaces, and/or accelerating drug passage through polar head groups to the lipid bilayer of cell membranes of target tissues. The additives of embodiments of the present invention have two parts that function together to facilitate rapid release of drug off the device surface and uptake by target tissue during deployment (by accelerating drug contact with tissues for which drug has high affinity) while preventing the premature release of drug from the device surface prior to device deployment at the target site.

In embodiments of the present invention, the therapeutic agent is rapidly released after the medical device is brought into contact with tissue and is readily absorbed. For example, certain embodiments of devices of the present invention include drug coated balloon catheters that deliver a lipophilic anti-proliferative pharmaceutical (such as paclitaxel or rapamycin) to vascular tissue through brief, direct pressure contact at high drug concentration during balloon angioplasty. The lipophilic drug is preferentially retained in target tissue at the delivery site, where it inhibits hyperplasia and restenosis yet allows endothelialization. In these embodiments, coating formulations of the present invention not only facilitate rapid release of drug from the balloon surface and transfer of drug into target tissues during deployment, but also prevent drug from diffusing away from the device during transit through tortuous arterial anatomy prior to reaching the target site and from exploding off the device during the initial phase of balloon inflation, before the drug coating is pressed into direct contact with the surface of the vessel wall.

The additive according to certain embodiments has a drug affinity part and a hydrophilic part. The drug affinity part is a hydrophobic part and/or has an affinity to the therapeutic agent by hydrogen bonding and/or van der Waals interactions. The drug affinity part may include aliphatic and aromatic organic hydrocarbon compounds, such as benzene, toluene, and alkanes, among others. These parts are not water soluble. They may bind both hydrophobic drug, with which they share structural similarities, and lipids of cell membranes. They have no covalently bonded iodine. The drug affinity part may include functional groups that can form hydrogen bonds with drug and with itself. The hydrophilic part may include hydroxyl groups, amine groups, amide groups, carbonyl groups, carboxylic acid and anhydrides, ethyl oxide, ethyl glycol, polyethylene glycol, ascorbic acid, amino acid, amino alcohol, glucose, sucrose, sorbitan, glycerol, polyalcohol, phosphates, sulfates, organic salts and their substituted molecules, among others. One or more hydroxyl, carboxyl, acid, amide or amine groups, for example, may be advantageous since they easily displace water molecules that are hydrogen-bound to polar head groups and surface proteins of cell membranes and may function to remove this barrier between hydrophobic drug and cell membrane lipid. These parts can dissolve in water and polar solvents. These additives are not oils, lipids, or polymers. The therapeutic agent is not enclosed in micelles or liposomes or encapsulated in polymer particles. The additive of embodiments of the present invention has components to both bind drug and facilitate its rapid movement off the medical device during deployment and into target tissues.

The additives in embodiments of the present invention are surfactants and chemical compounds with one or more hydroxyl, amino, carbonyl, carboxyl, acid, amide or ester moieties. The surfactants include ionic, nonionic, aliphatic, and aromatic surfactants. The chemical compounds with one or more hydroxyl, amino, carbonyl, carboxyl, acid, amide or ester moieties are chosen from amino alcohols, hydroxyl carboxylic acid and anhydrides, ethyl oxide, ethyl glycols, amino acids, peptides, proteins, sugars, glucose, sucrose, sorbitan, glycerol, polyalcohol, phosphates, sulfates, organic acids, esters, salts, vitamins, and their substituted molecules.

As is well known in the art, the terms "hydrophilic" and "hydrophobic" are relative terms. To function as an additive in exemplary embodiments of the present invention, the compound includes polar or charged hydrophilic moieties as well as non-polar hydrophobic (lipophilic) moieties.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute]octanol/[solute]water). Compounds with higher log Ps are more hydrophobic, while compounds with lower log Ps are more hydrophilic. Lipinski's rule suggests that pharmaceutical compounds having log P<5 are typically more membrane permeable. For purposes of certain embodiments of the present invention, it is preferable that the additive has log P less than log P of the drug to be formulated (as an example, log P of paclitaxel is 7.4). A greater log P difference between the drug and the additive can facilitate phase separation of drug. For example, if log P of the additive is much lower than log P of the drug, the additive may accelerate the release of drug in an aqueous environment from the surface of a device to which drug might otherwise tightly adhere, thereby accelerating drug delivery to tissue during brief deployment at the site of intervention. In certain embodiments of the present invention, log P of the additive is negative. In other embodiments, log P of the additive is less than log P of the drug. While a compound's octanol-water partition coefficient P or log P is useful as a measurement of relative hydrophilicity and hydrophobicity, it is merely a rough guide that may be useful in defining suitable additives for use in embodiments of the present invention.

Suitable additives that can be used in embodiments of the present invention include, without limitation, organic and inorganic pharmaceutical excipients, natural products and derivatives thereof (such as sugars, vitamins, amino acids, peptides, proteins, and fatty acids), low molecular weight oligomers, surfactants (anionic, cationic, non-ionic, and ionic), and mixtures thereof. The following detailed list of additives useful in the present invention is provided for exemplary purposes only and is not intended to be comprehensive. Many other additives may be useful for purposes of the present invention.

Surfactants

The surfactant can be any surfactant suitable for use in pharmaceutical compositions. Such surfactants can be anionic, cationic, zwitterionic or non-ionic. Mixtures of surfactants are also within the scope of the invention, as are combinations of surfactant and other additives. Surfactants often have one or more long aliphatic chains such as fatty acids that may insert directly into lipid bilayers of cell membranes to form part of the lipid structure, while other components of the surfactants loosen the lipid structure and enhance drug penetration and absorption. The contrast agent iopromide does not have these properties.

An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. In certain embodiments of the present invention, a higher HLB value is preferred, since increased hydrophilicity may facilitate release of hydrophobic drug from the surface of the device. In one embodiment, the HLB of the surfactant additive is higher than 10. In another embodiment, the additive HLB is higher than 14. Alternatively, surfactants having lower HLB may be preferred when used to prevent drug loss prior to device deployment at the target site, for example in a top coat over a drug layer that has a very hydrophilic additive.

It should be understood that the HLB value of a surfactant is merely a rough guide generally used to enable formulation of industrial, pharmaceutical and cosmetic emulsions, for example. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Keeping these inherent difficulties in mind, and using HLB values as a guide, surfactants may be identified that have suitable hydrophilicity or hydrophobicity for use in embodiments of the present invention, as described herein.

PEG-Fatty Acids and PEG-Fatty Acid Mono and Diesters

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful in embodiments of the present invention. Preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. The HLB values are in the range of 4-20.

Polyethylene glycol fatty acid diesters are also suitable for use as surfactants in the compositions of embodiments of the present invention. Most preferred hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present invention, including mixtures of two or more commercial surfactants as well as mixtures of surfactants with another additive or additives. Several PEG-fatty acid esters are marketed commercially as mixtures or mono- and diesters.

Polyethylene Glycol Glycerol Fatty Acid Esters

Preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products

A large number of surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil®b M 2735 CS), PEG-8 corn oil (Labrafil® WL 2609 BS), PEG-20 corn glycerides (Crovol M40), and PEG-20 almond glycerides (Crovol A40).

Polyglyceryl Fatty Acids

Polyglycerol esters of fatty acids are also suitable surfactants for use in embodiments of the present invention. Among the polyglyceryl fatty acid esters, preferred hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also preferred surfactants.

Propylene Glycol Fatty Acid Esters

Esters of propylene glycol and fatty acids are suitable surfactants for use in embodiments of the present invention. In this surfactant class, preferred hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800).

Sterol and Sterol Derivatives

Sterols and derivatives of sterols are suitable surfactants for use in embodiments of the present invention. Preferred derivatives include the polyethylene glycol derivatives. A preferred surfactant in this class is PEG-24 cholesterol ether (Solulan C-24).

Polyethylene Glycol Sorbitan Fatty Acid Esters

A variety of PEG-sorbitan fatty acid esters are available and are suitable for use as surfactants in embodiments of the present invention. Among the PEG-sorbitan fatty acid esters, preferred surfactants include PEG-20 sorbitan monolaurate (Tween-20), PEG-20 sorbitan monopalmitate (Tween-40), PEG-20 sorbitan monostearate (Tween-60). Laurate esters are preferred because they have a short lipid chain compared with oleate esters, increasing drug absorption.

Polyethylene Glycol Alkyl Ethers

Ethers of polyethylene glycol and alkyl alcohols are suitable surfactants for use in embodiments of the present invention. Preferred ethers include PEG-3 oleyl ether (Volpo 3) and PEG-4 lauryl ether (Brij 30).

Sugar and its Derivatives

Sugar derivatives are suitable surfactants for use in embodiments of the present invention. Preferred surfactants in this class include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, and octyl-β-D-thioglucopyranoside.

Polyethylene Glycol Alkyl Phenols

Several PEG-alkyl phenol surfactants are available, such as PEG-10-100 nonyl phenol and PEG-15-100 octyl phenol ether, Tyloxapol, octoxynol, nonoxynol, and are suitable for use in embodiments of the present invention.

Polyoxyethylene-Polyoxypropylene (POE-POP) Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula:

HO(C$_2$H$_4$O)$_a$(C$_3$H$_6$O)$_b$(C$_2$H$_4$O)$_a$H where "a" and "b" denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Sorbitan Fatty Acid Esters

Sorbitan esters of fatty acids are suitable surfactants for use in embodiments of the present invention. Among these esters, preferred hydrophobic surfactants include sorbitan monolaurate (Arlacel 20), sorbitan monopalmitate (Span-40), and sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). And second, when the pH increases so as to convert a fraction of the ascorbyl palmitate to a more soluble salt, such as sodium ascorbyl palmitate.

Ionic Surfactants

Ionic surfactants, including cationic, anionic and zwitterionic surfactants, are suitable hydrophilic surfactants for use in embodiments of the present invention. Preferred ionic surfactants include quaternary ammonium salts, fatty acid salts and bile salts. Specifically, preferred ionic surfactants include benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, and sodium taurocholate. These quaternary ammonium salts are preferred additives. They can be dissolved in both organic solvents (such as ethanol, acetone, and toluene) and water. This is especially useful for medical device coatings because it simplifies the preparation and coating process and has good adhesive properties. Water insoluble drugs are commonly dissolved in organic solvents.

Some of the surfactants described herein are very stable under heating. They survive an ethylene oxide sterilization process. They do not react with drugs such as paclitaxel or rapamycin under the sterilization process. The hydroxyl, ester, amide groups are preferred because they are unlikely to react with drug, while amine and acid groups often do react with paclitaxel or rapamycin during sterilization. Furthermore, surfactant additives improve the integrity and quality of the coating layer, so that particles do not fall off during handling. When the surfactants described herein are formulated with paclitaxel, experimentally it protects drug from premature release during the device delivery process while facilitating rapid release and elution of paclitaxel during a very brief deployment time of 0.2 to 2 minutes at the target site. Drug absorption by tissues at the target site is unexpectedly high experimentally.

Chemical Compounds with One or More Hydroxyl, Amino, Carbonyl, Carboxyl, Acid, Amide or Ester Moieties The chemical compounds with one or more hydroxyl, amino, carbonyl, carboxyl, acid, amide or ester moieties include amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohols and organic acids, and their substituted molecules. Hydrophilic chemical compounds with one or more hydroxyl, amino, carbonyl, carboxyl, acid, amide or ester moieties having a molecular weight less than 5,000-10,000 are preferred in certain embodiments. In other embodiments, molecular weight of the additive with one or more hydroxyl, amino, carbonyl, carboxyl, acid, amide, or ester moieties is preferably less than 1000-5,000, or more preferably less than 750-1,000, or most preferably less than 750. In these embodiments, the molecular weight of the additive is preferred to be less than that of the drug to be delivered. Further, the molecular weight of the additive is preferred to be higher than 80 since molecules with molecular weight less than 80 very easily evaporate and do not stay in the coating of a medical device. Small molecules can diffuse quickly. They can release themselves easily from the delivery balloon, accelerating release of drug, and they can diffuse away from drug when the drug binds tissue of the body lumen.

In certain embodiments, more than four hydroxyl groups are preferred, for example in the case of a high molecular weight additive. Large molecules diffuse slowly. If the molecular weight of the additive or the chemical compound is high, for example if the molecular weight is above 800, above 1000, above 1200, above 1500, or above 2000; large molecules may elute off of the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. The hydroxyl group is preferred as the hydrophilic moiety because it is unlikely to react with water insoluble drug, such as paclitaxel or rapamycin. In some embodiments, the chemical compound having more than four hydroxyl groups has a melting point of 120° C. or less. In some embodiments, the chemical compound having more than four hydroxyl groups has three adjacent hydroxyl groups that in stereo configuration are all on one side of the molecule. For example, sorbitol and xylitol have three adjacent hydroxyl groups that in stereoconfiguration are all on one side of the molecule, while galactitol does not. The difference impacts the physical properties of the isomers such as the melting temperature. The stereoconfiguration of the three adjacent hydroxyl groups may enhance drug binding. This will lead to improved compatibility of the water insoluble drug and hydrophilic additive, and improved tissue uptake and absorption of drug.

Some of the chemical compounds with one or more hydroxyl, amine, carbonyl, carboxyl, or ester moieties described herein are very stable under heating. They survive an ethylene oxide sterilization process and do not react with the water insoluble drug paclitaxel or rapamycin during sterilization. L-ascorbic acid and its salt and diethanolamine, on the other hand, do not necessarily survive such a sterilization process, and they react with paclitaxel. A different sterilization method is therefore preferred for L-ascorbic acid and diethanolamine. Hydroxyl, ester, and amide groups are preferred because they are unlikely to react with therapeutic agents such as paclitaxel or rapamycin. Sometimes, amine and acid groups do react with paclitaxel, for example, experimentally, benzoic acid, gentisic acid, diethanolamine, and ascorbic acid were not stable under ethylene oxide sterilization, heating, and aging process and reacted with paclitaxel. When the chemical compounds described herein are formulated with paclitaxel, a top coat layer may be advantageous in order to prevent premature drug loss during the device delivery process before deployment at the target site, since hydrophilic small molecules sometimes release drug too easily. The chemical compounds herein rapidly elute drug off the balloon during deployment at the target site. Surprisingly, even though some drug is lost during transit of the device to the target site when the coating contains these additives, experimentally drug absorption by tissue is unexpectedly high after only 0.2-2 minutes of deployment, for example, with the additive hydroxyl lactones such as ribonic acid lactone and gluconolactone.

Fat-Soluble Vitamins and Salts Thereof

Vitamins A, D, E and K in many of their various forms and provitamin forms are considered as fat-soluble vitamins and in addition to these a number of other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present invention.

The following examples of fat-soluble vitamin derivatives and/or sources are also useful as additives: Alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II). Folic acid is also of this type, and although it is water-soluble at physiological pH, it can be formulated in the free acid form. Other derivatives of fat-soluble vitamins useful in embodiments of the present invention may easily be obtained via well known chemical reactions with hydrophilic molecules.

Water-Soluble Vitamins and their Amphiphilic Derivatives

Vitamins B, C, U, pantothenic acid, folic acid, and some of the menadione-related vitamins/provitamins in many of their various forms are considered water-soluble vitamins. These may also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present invention. Salts of these can also be useful as additives in the present invention. Examples of water-soluble vitamins and derivatives include, without limitation, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present invention. The linkage of a palmitate chain to vitamin C yields ascorbyl palmitate.

Amino Acids and their Salts

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof are other useful additives in embodiments of the invention.

Certain amino acids, in their zwitterionic form and/or in a salt form with a monovalent or multivalent ion, have polar groups, relatively high octanol-water partition coefficients, and are useful in embodiments of the present invention. In the context of the present disclosure we take "low-solubility amino acid" to mean an amino acid which has a solubility in unbuffered water of less than about 4% (40 mg/ml). These include Cystine, tyrosine, tryptophan, leucine, isoleucine, phenylalanine, asparagine, aspartic acid, glutamic acid, and methionine.

Amino acid dimers, sugar-conjugates, and other derivatives are also useful. Through simple reactions well known in the art hydrophilic molecules may be joined to hydrophobic amino acids, or hydrophobic molecules to hydrophilic amino acids, to make additional additives useful in embodiments of the present invention.

Catecholamines, such as dopamine, levodopa, carbidopa, and DOPA, are also useful as additives.

Oligopeptides, Peptides and Proteins

Oligopeptides and peptides are useful as additives, since hydrophobic and hydrophilic amino acids may be easily coupled and various sequences of amino acids may be tested to maximally facilitate permeation of tissue by drug.

Proteins are also useful as additives in embodiments of the present invention. Serum albumin, for example, is a particularly preferred additive since it is water-soluble and contains significant hydrophobic parts to bind drug: paclitaxel is 89% to 98% protein-bound after human intravenous infusion, and rapamycin is 92% protein bound, primarily (97%) to albumin. Furthermore, paclitaxel solubility in PBS increases over 20-fold with the addition of BSA. Albumin is naturally present at high concentrations in serum and is thus very safe for human intravascular use.

Other useful proteins include, without limitation, other albumins, immunoglobulins, caseins, hemoglobins, lysozymes, immunoglobins, a-2-macroglobulin, fibronectins, vitronectins, firbinogens, lipases, and the like.

Organic Acids and their Esters and Anhydrides

Examples are acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, and 2-pyrrolidone.

These esters and anhydrides are soluble in organic solvents such as ethanol, acetone, methylethylketone, ethylacetate. The water insoluble drugs can be dissolved in organic solvent with these esters and anhydrides, then coated easily on to the medical device, then hydrolyzed under high pH conditions. The hydrolyzed anhydrides or esters are acids or alcohols, which are water soluble and can effectively carry the drugs off the device into the vessel walls.

Other Chemical Compounds with One or More Hydroxyl, Amine, Carbonyl, Carboxyl, or Ester Moieties The additives according to embodiments include amino alcohols, alcohols, amines, acids, amides and hydroxyl acids in both cyclo and linear aliphatic and aromatic groups. Examples are L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

Combinations of additives are also useful for purposes of the present invention.

One embodiment comprises the combination or mixture of two additives, for example, a first additive comprising a surfactant and a second additive comprising a chemical compound with one or more hydroxyl, amine, carbonyl, carboxyl, or ester moieties.

The combination or mixture of the surfactant and the small water-soluble molecule (the chemical compounds with one or more hydroxyl, amine, carbonyl, carboxyl, or ester moieties) has advantages. Formulations comprising mixtures of the two additives with water-insoluble drug are in certain cases superior to mixtures including either additive alone. The hydrophobic drugs bind extremely water-soluble small molecules more poorly than they do surfactants. They are often phase separated from the small water-soluble molecules, which can lead to suboptimal coating uniformity and integrity. The water-insoluble drug has Log P higher than both that of the surfactant and that of small water-soluble molecules. However, Log P of the surfactant is typically higher than Log P of the chemical compounds with one or more hydroxyl, amine, carbonyl, carboxyl, or ester moieties. The surfactant has a relatively high Log P (usually above 0) and the water soluble molecules have low Log P (usually below 0). Some surfactants, when used as additives in embodiments of the present invention, adhere so strongly to the water-insoluble drug and the surface of the medical device that drug is not able to rapidly release from the surface of the medical device at the target site. On the other hand, some of the water-soluble small molecules (with one or more hydroxyl, amine, carbonyl, carboxyl, or ester moieties) adhere so poorly to the medical device that they release drug before it reaches the target site, for example, into serum during the transit of a coated balloon catheter to the site targeted for intervention. Surpassingly, by adjusting the ratio of the concentrations of the small hydrophilic molecule and the surfactant in the formulation, the inventor has found that the coating stability during transit and rapid drug release when inflated and pressed against tissues of the lumen wall at the target site of therapeutic intervention in certain cases is superior to a formulation comprising either additive alone. Furthermore, the miscibility and compatibility of the water-insoluble drug and the highly water-soluble molecules is improved by the presence of the surfactant. The surfactant also improves coating uniformity and integrity by its good adhesion to the drug and the small molecules. The long chain hydrophobic part of the surfactant binds drug tightly while the hydrophilic part of the surfactant binds the water-soluble small molecules.

The surfactants in the mixture or the combination include all of the surfactants described herein for use in embodiments of the invention. The surfactant in the mixture may be chosen from PEG fatty esters, PEG omega-3 fatty esters and alcohols, glycerol fatty esters, sorbitan fatty esters, PEG glyceryl fatty esters, PEG sorbitan fatty esters, sugar fatty esters, PEG sugar esters, Tween 20, Tween 40, Tween 60, p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, Tween 20, Tween 40, Tween 60, Tween 80, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside and their derivatives.

The chemical compound with one or more hydroxyl, amine, carbonyl, carboxyl, or ester moieties in the mixture or the combination include all of the chemical compounds with one or more hydroxyl, amine, carbonyl, carboxyl, or ester moieties described herein for use in embodiments of the invention. The chemical compound with one or more hydroxyl, amine, carbonyl, carboxyl, or ester moieties in the mixture has at least one hydroxyl group in one of the embodiments in the inventions. In certain embodiments, more than four hydroxyl groups are preferred, for example in the case of a high molecular weight additive. In some embodiments, the chemical compound having more than four hydroxyl groups has a melting point of 120° C. or less. Large molecules diffuse slowly. If the molecular weight of the additive or the chemical compound is high, for example if the molecular weight is above 800, above 1000, above 1200, above 1500, or above 2000; large molecules may elute off of the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. The hydroxyl group is preferred as the hydrophilic moiety because it is unlikely to react with water insoluble drug, such as paclitaxel or rapamycin.

The chemical compound with one or more hydroxyl, amine, carbonyl, carboxyl, or ester moieties in the mixture is chosen from L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra (propylene glycol, and penta(propylene glycol), poly(propylene glycol) oligomers, a block copolymer of polyethylene glycol and polypropylene glycol, and derivatives and combinations thereof.

Mixtures or combinations of a surfactant and a water-soluble small molecule confer the advantages of both additives. The water insoluble drug often has a poor compatibility with highly water-soluble chemical compounds, and the surfactant improves compatibility. The surfactant also improves the coating quality, uniformity, and integrity, and particles do not fall off the balloon during handling. The surfactant reduces drug loss during transit to a target site. The water-soluble chemical compound improves the release of drug off the balloon and absorption of the drug in the tissue. Experimentally, the combination was surprisingly effective at preventing drug release during transit and achieving high drug levels in tissue after very brief 0.2-2 minute deployment. Furthermore, in animal studies it effectively reduced arterial stenosis and late lumen loss.

Some of the mixtures or combinations of surfactants and water-soluble small molecules are very stable under heating. They survived an ethylene oxide sterilization process and do not react with the water insoluble drug paclitaxel or rapamycin during sterilization. The hydroxyl, ester, amide groups are preferred because they are unlikely to react with therapeutic agents such as paclitaxel or rapamycin. Sometimes amine and acid groups do react with paclitaxel and are not stable under ethylene oxide sterilization, heating, and aging. When the mixtures or combinations described herein are formulated with paclitaxel, a top coat layer may be advantageous in order to protect the drug layer and from premature drug loss during the device.

Preferred additives include p-isononylphenoxypolyglycidol, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); cetotiamine; cyclothiamine, dexpanthenol, niacinamide, nicotinic acid and its salt, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta (ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof. (chemical compounds with one or more hydroxyl, amino, carbonyl, carboxyl, or ester moieties). Some of these additives are both water-soluble and organic solvent-soluble. They have good adhesive properties and adhere to the surface of polyamide medical devices, such as balloon catheters. They may therefore be used in the adherent layer, top layer, and/or in the drug layer of embodiments of the present invention. The aromatic and aliphatic groups increase the solubility of water insoluble drugs in the coating solution, and the polar groups of alcohols and acids accelerate drug permeation of tissue.

Other preferred additives according to embodiments of the invention include the combination or mixture or amide reaction products of an amino alcohol and an organic acid. Examples are lysine/glutamic acid, lysine acetate, lactobionic acid/meglumine, lactobionic acid/tromethanemine, lactobionic acid/diethanolamine, lactic acid/meglumine, lactic acid/tromethanemine, lactic acid/diethanolamine, gentisic acid/meglumine, gentisic acid/tromethanemine, gensitic acid/diethanolamine, vanillic acid/meglumine, vanillic acid/tromethanemine, vanillic acid/diethanolamine, benzoic acid/meglumine, benzoic acid/tromethanemine, benzoic acid/diethanolamine, acetic acid/meglumine, acetic acid/tromethanemine, and acetic acid/diethanolamine.

Other preferred additives according to embodiments of the invention include hydroxyl ketone, hydroxyl lactone, hydroxyl acid, hydroxyl ester, and hydroxyl amide. Examples are gluconolactone, D-glucoheptono-1,4-lactone, glucooctanoic lactone, gulonic acid lactone, mannoic lactone, erythronic acid lactone, ribonic acid lactone, glucuronic acid, gluconic acid, gentisic acid, lactobionic acid, lactic acid, acetaminophen, vanillic acid, sinapic acid, hydroxybenzoic acid, methyl paraben, propyl paraben, and derivatives thereof.

Other preferred additives that may be useful in embodiments of the present invention include riboflavin, riboflavin-phosphate sodium, Vitamin D3, folic acid (vitamin B9), vitamin 12, diethylenetriaminepentaacetic acid dianhydride, ethylenediaminetetraacetic dianhydride, maleic acid and anhydride, succinic acid and anhydride, diglycolic anhydride, glutaric anhydride, L-ascorbic acid, thiamine, nicotinamide, nicotinic acid, 2-pyrrolidone-5-carboxylic acid, cystine, tyrosine, tryptophan, leucine, isoleucine, phenylalanine, asparagine, aspartic acid, glutamic acid, and methionine.

From a structural point of view, these additives share structural similarities and are compatible with water insoluble drugs (such as paclitaxel and rapamycin). They often contain double bonds such as $C=C$, $C=N$, $C=O$ in aromatic or aliphatic structures. These additives also contain amine, alcohol, ester, amide, anhydride, carboxylic acid, and/or hydroxyl groups. They may form hydrogen bonds and/or van der Waals interactions with drug. They are also useful in the top layer in the coating. Compounds containing one or more hydroxyl, carboxyl, or amine groups, for example, are especially useful as additives since they facilitate drug release from the device surface and easily displace water next to the polar head groups and surface proteins of cell membranes and may thereby remove this barrier to hydrophobic drug permeability. They accelerate movement of a hydrophobic drug off the balloon to the lipid layer of cell membranes and tissues for which it has very high affinity. They may also carry or accelerate the movement of drug off the balloon into more aqueous environments such as the interstitial space, for example, of vascular tissues that have been injured by balloon angioplasty or stent expansion. Additives such as polyglyceryl fatty esters, ascorbic ester of fatty acids, sugar esters, alcohols and ethers of fatty acids have fatty chains that can integrate into the lipid structure of target tissue membranes, carrying drug to lipid structures. Some of the amino acids, vitamins and organic acids have aromatic $C=N$ groups as well as amino, hydroxyl, and carboxylic components to their structure. They have structural parts that can bind or complex with hydrophobic drug, such as paclitaxel or rapamycin, and they also have structural parts that facilitate tissue penetration by removing barriers between hydrophobic drug and lipid structure of cell membranes.

For example, isononylphenylpolyglycidol (Olin-10 G and Surfactant-10G), PEG glyceryl monooleate, sorbitan monolaurate (Arlacel 20), sorbitan monopalmitate (Span-40), sorbitan monooleate (Span-80), sorbitan monostearate, polyglyceryl-10 oleate, polyglyceryl-10 laurate, polyglyceryl-10 palmitate, and polyglyceryl-10 stearate all have more than four hydroxyl groups in their hydrophilic part. These hydroxyl groups have very good affinity for the vessel wall and can displace hydrogen-bound water molecules. At the same time, they have long chains of fatty acid, alcohol, ether and ester that can both complex with hydrophobic drug and integrate into the lipid structure of the cell membranes to form the part of the lipid structure. This deformation or loosening of the lipid membrane of target cells may further accelerate permeation of hydrophobic drug into tissue.

For another example, L-ascorbic acid, thiamine, maleic acids, niacinamide, and 2-pyrrolidone-5-carboxylic acid all have a very high water and ethanol solubility and a low molecular weight and small size. They also have structural components including aromatic $C=N$, amino, hydroxyl, and carboxylic groups. These structures have very good compatibility with paclitaxel and rapamycin and can increase the solubility of these water-insoluble drugs in water and enhance their absorption into tissues. However, they often have poor adhesion to the surface of medical devices. They are therefore preferably used in combination with other additives in the drug layer and top layer where they are useful to enhance drug absorption. Vitamin D2 and D3 are especially useful because they themselves have anti-restenotic effects and reduce thrombosis, especially when used in combination with paclitaxel.

In embodiments of the present invention, the additive is soluble in aqueous solvents and is soluble in organic solvents. Extremely hydrophobic compounds that lack sufficient hydrophilic parts and are insoluble in aqueous solvent, such as the dye Sudan Red, are not useful as additives in these embodiments. Sudan red is also genotoxic.

In one embodiment, the concentration density of the at least one therapeutic agent applied to the surface of the medical device is from about 1 to 20 µg/mm$^2$, or more preferably from about 2 to 6 µg/mm$^2$. In one embodiment, the concentration of the at least one additive applied to the surface of the medical device is from about 1 to 20 µg/mm$^2$. The ratio of additives to drug by weight in the coating layer in embodiments of the present invention is about 20 to 0.05, preferably about 10 to 0.5, or more preferably about 5 to 0.8.

The relative amount of the therapeutic agent and the additive in the coating layer may vary depending on applicable circumstances. The optimal amount of the additive can depend upon, for example, the particular therapeutic agent and additive selected, the critical micelle concentration of the surface modifier if it forms micelles, the hydrophilic-lipophilic-balance (HLB) of a surfactant or an additive's octonol-water partition coefficient (P), the melting point of the additive, the water solubility of the additive and/or therapeutic agent, the surface tension of water solutions of the surface modifier, etc.

The additives are present in exemplary coating compositions of embodiments of the present invention in amounts such that upon dilution with an aqueous solution, the carrier forms a clear, aqueous dispersion or emulsion or solution, containing the hydrophobic therapeutic agent in aqueous and organic solutions. When the relative amount of surfactant is too great, the resulting dispersion is visibly "cloudy".

The optical clarity of the aqueous dispersion can be measured using standard quantitative techniques for turbidity assessment. One convenient procedure to measure turbidity is to measure the amount of light of a given wavelength transmitted by the solution, using, for example, an UV-visible spectrophotometer. Using this measure, optical clarity corresponds to high transmittance, since cloudier solutions will scatter more of the incident radiation, resulting in lower transmittance measurements.

Another method of determining optical clarity and carrier diffusivity through the aqueous boundary layer is to quantitatively measure the size of the particles of which the dispersion is composed. These measurements can be performed on commercially available particle size analyzers.

Other considerations will further inform the choice of specific proportions of different additives. These considerations include the degree of bioacceptability of the additives and the desired dosage of hydrophobic therapeutic agent to be provided.

Therapeutic Agent

The drugs or biologically active materials, which can be used in embodiments of the present invention, can be any therapeutic agent or substance. The drugs can be of various physical states, e.g., molecular distribution, crystal forms or cluster forms. Examples of drugs that are especially useful in embodiments of the present invention are lipophilic substantially water insoluble drugs, such as paclitaxel, rapamycin, daunorubicin, doxorubicin, lapachone, vitamin D2 and D3 and analogues and derivatives thereof. These drugs are especially suitable for use in a coating on a balloon catheter used to treat tissue of the vasculature.

Other drugs that may be useful in embodiments of the present invention include, without limitation, glucocorticoids (e.g., dexamethasone, betamethasone), hirudin, angiopeptin, aspirin, growth factors, antisense agents, anti-cancer agents, anti-proliferative agents, oligonucleotides, and, more generally, anti-platelet agents, anti-coagulant agents, anti-mitotic agents, antioxidants, anti-metabolite agents, anti-chemotactic, and anti-inflammatory agents.

Also useful in embodiments of the present invention are polynucleotides, antisense, RNAi, or siRNA, for example, that inhibit inflammation and/or smooth muscle cell or fibroblast proliferation.

Anti-platelet agents can include drugs such as aspirin and dipyridamole. Aspirin is classified as an analgesic, antipyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in embodiments of the present invention can include drugs such as heparin, protamine, hirudin and tick anticoagulant protein. Anti-oxidant agents can include probucol. Anti-proliferative agents can include drugs such as amlodipine and doxazosin. Anti-mitotic agents and anti-metabolite agents that can be used in embodiments of the present invention include drugs such as methotrexate, azathioprine, vincristine, vinblastine, 5-fluorouracil, adriamycin, and mutamycin. Antibiotic agents for use in embodiments of the present invention include penicillin, cefoxitin, oxacillin, tobramycin, and gentamicin. Suitable antioxidants for use in embodiments of the present invention include probucol. Additionally, genes or nucleic acids, or portions thereof can be used as the therapeutic agent in embodiments of the present invention. Furthermore, collagen-synthesis inhibitors, such as tranilast, can be used as a therapeutic agent in embodiments of the present invention.

Photosensitizing agents for photodynamic or radiation therapy, including various porphyrin compounds such as porfimer, for example, are also useful as drugs in embodiments of the present invention.

Drugs for use in embodiments of the present invention also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, .beta.-sitosterin, ademetionine, myrtecaine, polidocanol, nonivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon a, .beta and y, histamine antagonists, serotonin blockers, apoptosis inhibitors, apoptosis regulators such as p65 NF-kB or Bcl-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamide, retinoic acid, quinidine, disopyramide, flecamide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestain A and B, cudraisoflavonei A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyryl-mallotochromanol, maquiroside A, marchantin A, maytansine, lycoridicin, margetine, pancratistatin, liriodenine, bisparthenolidine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, and vismione A and B.

A combination of drugs can also be used in embodiments of the present invention. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations may reduce complications from using a high dose of the drug.

Adherent Layer

The adherent layer, which is an optional layer underlying the drug coating layer, improves the adherence of the drug coating layer to the exterior surface of the medical device and protects coating integrity. If drug and additive differ in their adherence to the medical device, the adherent layer may prevent differential loss (during transit) or elution (at the target site) of drug layer components in order to maintain consistent drug-to-additive or drug-to-drug ratio in the drug layer and therapeutic delivery at the target site of intervention. Furthermore, the adherent layer may function to facilitate release of coating layer components which otherwise might adhere too strongly to the device for elution during brief contact with tissues at the target site. For example, in the case where a particular drug binds the medical device tightly, more hydrophilic components are incorporated into the adherent layer in order to decrease affinity of the drug to the device surface.

As described above, the adherent layer comprises a polymer or an additive or mixtures of both. The polymers that are useful for forming the adherent layer are ones that are biocompatible and avoid irritation of body tissue. Some examples of polymers that are useful for forming the adherent layer are polymers that are biostable, such as polyurethanes, silicones, and polyesters. Other polymers that are useful for forming the adherent layer include polymers that can be dissolved and polymerized on the medical device.

Some examples of polymers that are useful in the adherent layer of embodiments of the present invention include polyolefins, polyisobutylene, ethylene-1-olefin copolymers, acrylic polymers and copolymers, polyvinyl chloride, polyvinyl methyl ether, polyvinylidene fluoride and polyvinylidene chloride, polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyethers, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, and mixtures and block copolymers thereof.

Since the medical device undergoes mechanical manipulation, i.e., expansion and contraction, examples of polymers that are useful in the adherent layer include elastomeric polymers, such as silicones (e.g., polysiloxanes and substituted polysiloxanes), polyurethanes, thermoplastic elastomers, ethylene vinyl acetate copolymers, polyolefin elastomers, and EPDM rubbers. Due to the elastic nature of these polymers, when these polymers are used, the coating better adheres to the surface of the medical device when the device is subjected to forces or stress.

The adherent layer may also comprise one or more of the additives previously described, or other components, in order to maintain the integrity and adherence of the coating layer to the device and to facilitate both adherence of drug and additive components during transit and rapid elution during deployment at the site of therapeutic intervention.

Top Layer

In order to further protect the integrity of the drug layer, an optional top layer may be applied to prevent loss of drug during transit through tortuous anatomy to the target site or during the initial expansion of the device before the coating makes direct contact with target tissue. The top layer may release slowly in the body lumen while protecting the drug layer. The top layer will erode more slowly if it is comprised of more hydrophobic, high molecular weight additives. Surfactants are examples of more hydrophobic structures with long fatty chains, such as Tween 20 and polyglyceryl oleate. High molecular weight additives include polyethylene oxide, polyethylene glycol, and polyvinyl pyrrolidone. Hydrophobic drug itself can act as a top layer component. For example, paclitaxel or rapamycin are hydrophobic. They can be used in the top layer. On the other hand, the top layer cannot erode too slowly or it might actually slow the release of drug during deployment at the target site. Other additives useful in the top coat include additives that strongly interact with drug or with the coating layer, such as p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

Solvents

Solvents for preparing of the coating layer may include, as examples, any combination of one or more of the following: (a) water, (b) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) mixture of water and organic solvents such as water/ethanol, water/acetone, water/methanol, water/tetrahydrofuran. A preferred solvent in the top coating layer is acetone.

Organic solvents, such as short-chained alcohol, dioxane, tetrahydrofuran, dimethylformamide, acetonitrile, dimethylsulfoxide, etc., are particularly useful and preferred solvents in embodiments of the present invention because these organic solvents generally disrupt collodial aggregates and co-solubilize all the components in the coating solution.

The therapeutic agent and additive or additives may be dispersed in, solubilized, or otherwise mixed in the solvent. The weight percent of drug and additives in the solvent may be in the range of 0.1-80% by weight, preferably 2-20% by weight.

Another embodiment of the invention relates to a method for preparing a medical device, particularly, for example, a balloon catheter or a stent. First, a coating solution or suspension comprising at least one solvent, at least one therapeutic agent, and at least one additive is prepared. In at least one embodiment, the coating solution or suspension includes only these three components. The content of the therapeutic agent in the coating solution can be from 0.5-50% by weight based on the total weight of the solution. The content of the additive in the coating solution can be from 1-45% by weight, 1 to 40% by weight, or from 1-15% by weight based on the total weight of the solution. The amount of solvent used depends on the coating process and viscosity. It will affect the uniformity of the drug-additive coating but will be evaporated.

In other embodiments, two or more solvents, two or more therapeutic agents, and/or two or more additives may be used in the coating solution.

In other embodiments, a therapeutic agent, an additive and a polymeric material may be used in the coating solution, for example in a stent coating. In the coating, the therapeutic agent is not encapsulated in polymer particles.

Various techniques may be used for applying a coating solution to a medical device such as casting, spinning, spraying, dipping (immersing), ink jet printing, electrostatic techniques, and combinations of these processes. Choosing an application technique principally depends on the viscosity and surface tension of the solution. In embodiments of the present invention, dipping and spraying are preferred because it makes it easier to control the uniformity of the thickness of the coating layer as well as the concentration of the therapeutic agent applied to the medical device. Regardless of whether the coating is applied by spraying or by dipping or by another method or combination of methods, each layer is usually deposited on the medical device in multiple application steps in order to control the uniformity and the amount of therapeutic substance and additive applied to the medical device.

Each applied layer is from about 0.1 microns to 15 microns in thickness. The total number of layers applied to the medical device is in a range of from about 2 to 50. The total thickness of the coating is from about 2 to 200 microns.

As discussed above, spraying and dipping are particularly useful coating techniques for use in embodiments of the present invention. In a spraying technique, a coating solution or suspension of an embodiment of the present invention is prepared and then transferred to an application device for applying the coating solution or suspension to a balloon catheter.

An application device that may be used is a paint jar attached to an air brush, such as a Badger Model 150, supplied with a source of pressurized air through a regulator (Norgren, 0-160 psi). When using such an application device, once the brush hose is attached to the source of compressed air downstream of the regulator, the air is applied. The pressure is adjusted to approximately 15-25 psi and the nozzle condition checked by depressing the trigger.

Prior to spraying, both ends of the relaxed balloon are fastened to the fixture by two resilient retainers, i.e., alligator clips, and the distance between the clips is adjusted so that the balloon remained in a deflated, folded, or an inflated or partially inflated, unfolded condition. The rotor is then energized and the spin speed adjusted to the desired coating speed, about 40 rpm.

With the balloon rotating in a substantially horizontal plane, the spray nozzle is adjusted so that the distance from the nozzle to the balloon is about 1-4 inches. First, the coating solution is sprayed substantially horizontally with the brush being directed along the balloon from the distal end of the balloon to the proximal end and then from the proximal end to the distal end in a sweeping motion at a speed such that one spray cycle occurred in about three balloon rotations. The balloon is repeatedly sprayed with the coating solution, followed by drying, until an effective amount of the drug is deposited on the balloon.

In one embodiment of the present invention, the balloon is inflated or partially inflated, the coating solution is applied to the inflated balloon, for example by spraying, and then the balloon is deflated and folded before drying. Drying may be performed under vacuum.

It should be understood that this description of an application device, fixture, and spraying technique is exemplary only. Any other suitable spraying or other technique may be used for coating the medical device, particularly for coating the balloon of a balloon catheter or stent delivery system or stent.

After the medical device is sprayed with the coating solution, the coated balloon is subjected to a drying in which the solvent in the coating solution is evaporated. This produces a coating matrix on the balloon containing the therapeutic agent. One example of a drying technique is placing a coated balloon into an oven at approximately 20° C. or higher for approximately 24 hours. Any other suitable method of drying the coating solution may be used. The time and temperature may vary with particular additives and therapeutic agents.

Optional Post Treatment

After depositing the drug-additive containing layer on the device of certain embodiments of the present invention, dimethyl sulfoxide (DMSO) or other solvent may be applied, by dip or spray or other method, to the finished surface of the coating. DMSO readily dissolves drugs and easily penetrates membranes and may enhance tissue absorption.

It is contemplated that the medical devices of embodiments of the present invention have applicability for treating blockages and occlusions of any body passageways, including, among others, the vasculature, including coronary, peripheral, and cerebral vasculature, the gastrointestinal tract, including the esophagus, stomach, small intestine, and colon, the pulmonary airways, including the trachea, bronchi, bronchioles, the sinus, the biliary tract, the urinary tract, prostate and brain passages. They are especially suited for treating tissue of the vasculature with, for example, a balloon catheter or a stent.

Yet another embodiment of the present invention relates to a method of treating a blood vessel. The method includes inserting a medical device comprising a coating into a blood vessel. The coating layer comprises a therapeutic agent and an additive. In this embodiment, the medical device can be configured as having at least an expandable portion. Some examples of such devices include balloon catheters, perfusion balloon catheters, an infusion catheter such as distal perforated drug infusion catheters, a perforated balloon, spaced double balloon, porous balloon, and weeping balloon, cutting balloon catheters, scoring balloon catheters, self-expanded and balloon expanded-stents, guide catheters, guide wires, embolic protection devices, and various imaging devices.

As mentioned above, one example of a medical device that is particularly useful in the present invention is a coated balloon catheter. A balloon catheter typically has a long, narrow, hollow tube tabbed with a miniature, deflated balloon. In embodiments of the present invention, the balloon is coated with a drug solution. Then, the balloon is maneuvered through the cardiovascular system to the site of a blockage, occlusion, or other tissue requiring a therapeutic agent. Once in the proper position, the balloon is inflated and contacts the walls of the blood vessel and/or a blockage or occlusion. It is an object of embodiments of the present invention to rapidly deliver drug to and facilitate absorption by target tissue. It is advantageous to efficiently deliver drug to tissue in as brief a period of time as possible while the device is deployed at the target site. The therapeutic agent is released into such tissue, for example the vessel walls, in about 0.1 to 30 minutes, for example, or preferably about 0.1 to 10 minutes, or more preferably about 0.2 to 2 minutes, or most preferably, about 0.1 to 1 minutes, of balloon inflation time pressing the drug coating into contact with diseased vascular tissue.

Given that a therapeutically effective amount of the drug can be delivered by embodiments of the present invention into, for example, the arterial wall, in some cases the need for a stent may be eliminated, obviating the complications of fracture and thrombosis associated therewith.

Should placement of a stent still be desired, a particularly preferred use for embodiments of the present invention is to crimp a stent, such as a bare metal stent (BMS), for example, over the drug coated balloon described in embodiments herein. When the balloon is inflated to deploy the stent at the site of diseased vasculature, an effective amount of drug is delivered into the arterial wall to prevent or decrease the severity of restenosis or other complications. Alternatively, the stent and balloon may be coated together, or the stent may be coated and then crimped on a balloon.

Further, the balloon catheter may be used to treat vascular tissue/disease alone or in combination with other methods for treating the vasculature, for example, photodynamic therapy or atherectomy. Atherectomy is a procedure to remove plaque from arteries. Specifically, atherectomy removes plaque from peripheral and coronary arteries. The medical device used for peripheral or coronary atherectomy may be a laser catheter or a rotablator or a direct atherectomy device on the end of a catheter. The catheter is inserted into the body and advanced through an artery to the area of narrowing. After the atherectomy has removed some of the plaque, balloon angioplasty using the coated balloon of embodiments of the present invention may be performed. In addition, stenting may be performed thereafter, or simultaneous with expansion of the coated balloon as described above. Photodynamic therapy is a procedure where light or irradiated energy is used to kill target cells in a patient. A light-activated photosensitizing drug may be delivered to specific areas of tissue by embodiments of the present invention. A targeted light or radiation source selectively activates the drug to produce a cytotoxic response and mediate a therapeutic anti-proliferative effect.

In some of the embodiments of drug-containing coatings and layers according to the present invention, the coating or layer does not include polymers, oils, or lipids. And, furthermore, the therapeutic agent is not encapsulated in polymer particles, micelles, or liposomes. As described above, such formulations have significant disadvantages and can inhibit the intended efficient, rapid release and tissue penetration of the agent, especially in the environment of diseased tissue of the vasculature.

Although various embodiments are specifically illustrated and described herein, it will be appreciated that modifications and variations of the present invention are covered by the above teachings and are within the purview of the appended claims without departing from the spirit and intended scope of the invention.

Other than the operating examples, or where otherwise indicated, all numbers expressing quantities of components in a layer, reaction conditions, and so forth used in the specification and claims are to be understood as being modified in all instances by the term "about." Accordingly, unless otherwise indicated to the contrary, the numerical parameters set forth in this specification and attached claims are approximations that may vary depending upon the desired properties sought to be obtained by the present disclosure.

Preparation

The medical device and the coating layers of embodiments of the present invention can be made according to various methods. For example, the coating solution can be prepared by dispersing, dissolving, diffusing, or otherwise mixing all the ingredients, such as a therapeutic agent, an additive, and a solvent, simultaneously together. Also, the coating solution can be prepared by sequentially adding each component based on solubility or any other parameters. For example, the coating solution can be prepared by first adding the therapeutic agent to the solvent and then adding the additive. Alternatively, the additive can be added to the solvent first and then the therapeutic agent can be later added. If the solvent used does not sufficiently dissolve the drug, it is preferable to first add the additive to the solvent, then the drug, since the additive will increase drug solubility in the solvent.

EXAMPLES

The following examples include embodiments of medical devices and coating layers within the scope of the present invention. While the following examples are considered to embody the present invention, the examples should not be interpreted as limitations upon the present invention.

Example 1

Preparation of Coating Solutions

Formulation 1—50-150 mg (0.06-0.18 mmole) paclitaxel, 2-6 ml acetone (or ethanol), 25-100 mg ascorbyl palmitate, 25-100 mg L-ascorbic acid and 0.5 ml ethanol were mixed.

Formulation 2—50-150 mg (0.05-0.16 mmole) rapamycin, 2-6 ml acetone (or ethanol), 50-200 mg polyglyceryl-10 oleate and 0.5 ml ethanol were wemixed.

Formulation 3—50-150 mg (0.06-0.18 mmole) paclitaxel, 2-6 ml acetone (or ethanol), 50-200 mg octoxynol-9 and 0.5 ml ethanol were mixed.

Formulation 4—50-150 mg (0.05-0.16 mmole) rapamycin, 2-6 ml acetone (or ethanol), 50-200 mg p-isononylphenoxypolyglycidol and 0.5 ml ethanol were mixed.

Formulation 5—50-150 mg (0.06-0.18 mmole) paclitaxel, 2-6 ml acetone (or ethanol), 50-200 mg Tyloxapol and 0.5 ml ethanol were mixed.

Formulation 6—50-150 mg (0.05-0.16 mmole) rapamycin in 2-6 ml acetone (or ethanol), 50-150 mg L-ascorbic acid in 1 ml water or ethanol, both, then were mixed.

Formulation 7—50-150 mg (0.06-0.18 mmole) paclitaxel, 2-6 ml acetone (or ethanol), 50-150 mg niacinamide in 1 ml water or ethanol, were mixed.

Formulation 8—50-150 mg (0.05-0.16 mmole) rapamycin, 2-6 ml acetone (or ethanol), 50-200 mg nicotinic acid in 1 ml water or ethanol, were mixed.

Formulation 9—50-150 mg (0.06-0.18 mmole) paclitaxel, 2-6 ml ethanol (or acetone), 150 mg thiamine hydrochloride in 1 ml water, and 0.5 ml were mixed.

Formulation 10—50-150 mg (0.05-0.16 mmole) rapamycin, 2-6 ml acetone or ethanol, 150 mg 2-pyrrolidone-5-carboxylic acid in 1 ml water or ethanol, awere mixed.

Formulation 11—50-150 mg (0.06-0.18 mmole) paclitaxel, 2-6 ml acetone (or ethanol), 75 mg p-isononylphenoxypolyglycidol, 75 mg niacinamide in 1 ml water or ethanol, and 0.5 ml ethanol were mixed.

Formulation 12—50-150 mg (0.05-0.16 mmole) rapamycin, 2-6 ml acetone (or ethanol), 75 mg Octoxynol-9, 75 mg thiamine hydrochloride in 1 ml water or ethanol, and 0.5 ml ethanol were mixed.

Formulation 13—50-150 mg (0.06-0.18 mmole) paclitaxel, 2-6 ml acetone (or ethanol), 75 mg p-isononylphenoxypolyglycidol, 75 mg 2-pyrrolidone-5-carboxylic acid in 1 ml water or ethanol, and 0.5 ml ethanol were mixed.

Formulation 14—50-150 mg (0.06-0.18 mmole) paclitaxel, 2-6 ml acetone (or ethanol), 75 mg p-isononylphenoxypolyglycidol, 75 mg nicotinic acid in 1 ml water or ethanol, and 0.5 ml ethanol were mixed.

Formulation 15 50-150 mg (0.06-0.18 mmole) paclitaxel, 2-6 ml acetone (or ethanol), 75 mg p-isononylphenoxypolyglycidol, 75 mg L-ascorbic acid in 1 ml water or ethanol, and 0.5 ml ethanol were mixed.

Formulation 16 50-150 mg (0.06-0.18 mmole) paclitaxel was dissolved in 5-10 ml methylene chloride. The solution was added to 30 ml of human serum albumin solution (5% w/v). The solution was then homogenized for 5 minutes at low speed to form an emulsion. The emulsion was then sonicated at 40 kHz at 50-90% power at 0 to 5° C. for 1 to 5 min.

Formulation 17—50-150 mg (0.05-0.16 mmole) rapamycin was dissolved in 5-10 ml methylene chloride and 10-30 mg p-isononylphenoxypolyglycidol. The solution was added to 30 ml of human serum albumin solution (5% w/v). The solution was then homogenized for 5 minutes at low speed to form an emulsion. The emulsion was then sonicated at 40 kHz at 50-90% power at 0 to 5° C. for 1 to 5 min.

Formulation 18—50-100 mg (0.06-0.12 mmole) paclitaxel, 1-1.6 ml acetone, 1-1.6 ml ethanol, 0.4-1.0 ml water, and 50-200 mg gluconolactone were mixed.

Formulation 19—35-70 mg (0.042-0.084 mmole) paclitaxel, 0.5-1.0 ml acetone, 0.5-1.0 ml ethanol, 35-70 mg Tween 20, and 35-70 mg N-octanoyl N-methylglucamine were mixed.

Formulation 20—35-70 mg (0.042-0.084 mmole) paclitaxel, 0.4-1.0 ml acetone, 0.4-1.0 ml ethanol, 0.2-0.4 ml water, 35-70 mg Tween 20, and 35-70 mg sorbitol were mixed.

Formulation 21—40-80 mg (0.048-0.096 mmole) paclitaxel, 0.5-1.0 ml acetone, 0.5-1.0 ml ethanol, 40-80 mg meglumine, and 32-64 mg gensitic acid (equal molar ratio with meglumine) were mixed.

Formulation 22—35-70 mg (0.042-0.084 mmole) paclitaxel, 0.4-0.8 ml acetone, 0.4-0.8 ml ethanol, 0.25-0.50 ml water, 35-70 mg lactobionic acid, and 10-20 mg diethanolamine (equal molar ratio with lactobionic acid) were mixed.

Formulation 23—35-70 mg (0.042-0.084 mmole) paclitaxel, 0.5-1.0 ml acetone, 0.5-1.0 ml ethanol, and 70-140 mg N-octanoyl N-methylglucamine were mixed.

Formulation 24—35-70 mg (0.042-0.084 mmole) paclitaxel, 0.4-0.8 ml acetone, 0.4-0.8 ml ethanol, 0.2-0.4 ml water, 35-70 mg meglumine, and 18-36 mg lactic acid (equal molar ratio with meglumine) were mixed.

Formulation 25—50-100 mg (0.06-0.12 mmole) paclitaxel, 0.8-1.6 ml acetone, 0.8-1.6 ml ethanol, 0.4-1.0 ml water, 50-100 mg gensitic acid, and 30-60 mg diethanolamine (equal molar ratio with gensitic acid) were mixed.

Formulation 26—Comparison solution-50 mg (0.06 mmole) paclitaxel, 1 ml ethanol, 0.2 ml acetone, 0.042 ml Ultravist 370 were mixed.

Formulation 27—Comparison solution-40 mg (0.048 mmole) paclitaxel, 0.5 ml ethanol, 0.5 ml acetone were mixed.

Formulation 28—35-70 mg (0.042-0.084 mmole) paclitaxel, 0.5-1.0 ml acetone, 0.5-1.0 ml ethanol, 35-70 mg Triton X-100, and 35-70 mg N-heptanoyl N-methylglucamine were mixed.

Example 2

5 PTCA balloon catheters (3 mm in diameter and 20 mm in length) were folded with three wings under vacuum. The folded balloon under vacuum was sprayed or dipped in a formulation (1-17) in example 1. The folded balloon was then dried, sprayed or dipped again, dried again, and sprayed or dipped again until sufficient amount of drug on the balloon (3 microgram per square mm) was obtained. The coated folded balloon was then rewrapped and sterilized for animal testing.

Example 3

5 PTCA balloon catheters (3 mm in diameter and 20 mm in length) was folded with three wings under vacuum. The folded balloon under vacuum was sprayed or dipped in a formulation (1-5) in example 1. The folded balloon was then dried, sprayed or dipped again in a formulation (6-10), dried, and sprayed or dipped again until sufficient amount of drug on the balloon (3 microgram per square mm) was obtained. The coated folded balloon was then rewrapped and sterilized for animal testing.

Example 4

5 PTCA balloon catheters crimped with bare metal coronary stent (3 mm in diameter and 20 mm in length) were sprayed or dipped in a formulation (1-5) in example 1. The stent delivery system was then dried, sprayed or dipped again in a formulation (6-10), dried and sprayed or dipped again until sufficient amount of drug on the stent and balloon (3 microgram per square mm) is obtained. The coated folded stent delivery system was then sterilized for animal testing.

Example 5

Drug coated balloon catheters and uncoated balloon catheters (as control) were inserted into coronary arteries in pigs. The balloon was over dilated (1:1.2), and the inflated balloon was held in the vessel for 60 seconds to release drug and additive, then deflated and withdraw from the pig. The animals were angiographed after 3 days, 31 days, 3 months, 6 months, 9 months and 12 months. The amount of drug in the artery tissues of the sacrificed animal was measured after 60 minutes, 3 days, 31 days, 3 months, 6 months, 9 months and 12 months.

Example 6

5 coronary stents (3 mm in diameter and 18 mm in length) were spray or dip coated with the formulation (1-17) in example 1. The stents were then dried, sprayed or dipped again, and dried again until a sufficient amount of drug on the stent (3 microgram per square mm) is obtained. The coated stent was then crimped on PTCA balloon catheters (3 mm in diameters and 20 mm in length). The coated stents with balloon catheters were then sterilized for animal testing.

Example 7

The drug coated stent and uncoated stent (as control) were inserted into coronary arteries in pigs, then the balloon was over dilated (1:1.2). The stent was implanted and drug and additive released, and the balloon was deflated and withdrawn from the pig. The animals were then angiographed after 5, 30, 60 minutes, 3 days, 31 days, 3 months, 6 months, 9 months and 12 months. The amount of drug in the artery tissues of the sacrificed animal was measured 60 minutes, 1 day, 3 days, 31 days, 3 months, 6 months, 9 months and 12 months.

Example 8

5 PTCA balloon catheters were sprayed or dipped in the formulation (1-17) in example 1, dried, and sprayed or dipped and dried again until sufficient amount of drug on balloon is obtained (3 microgram per square mm) was obtained. A bare metal coronary stent (3 mm in diameter and 20 mm in length) was crimped on each coated balloon. The coated balloons with crimped bare metal stents were then wrapped and sterilized for animal test.

Example 9

5 PTCA balloon catheters were sprayed or dipped in a formulation (1-5) in example 1, dried, and sprayed or dipped again in a formulation (6-10). Balloons were then dried and sprayed or dipped again until sufficient amount of drug on the balloon (3 microgram per square mm) was obtained. A bare metal coronary stent (3 mm in diameter and 20 mm in length) was crimped on each coated balloon. The coated balloons with crimped bare metal stents were then wrapped and sterilized for animal test.

Example 10

The drug coated balloon-expandable bare metal stent of Examples 8 and 9 and plain balloon-expandable bare metal stent (as control) were inserted into coronary arteries in pigs, and the balloon is over dilated (1:1.2). Stent is implanted, and the balloon was held inflated for 60 seconds to release drug and additive, and the balloon was deflated and withdraw from the pig. The animals were then angiographed after 5, 30, 60 minutes, 3 days, 31 days, 3 months, 6 months, 9 months and 12 months. The amount of drug in the artery tissues of the sacrificed animal is measured after 60 minutes, 1 day, 3 days, 31 days, 3 months, 6 months, 9 months and 12 months.

Example 11

150 mg (0.18 mmole) paclitaxel, 5 ml acetone (or ethylacetate or methyl ethyl ketone), 150 mg acetic anhydride or maleic anhydride or diglycolic anhydride and 0.5 ml ethanol were mixed, then stirred until a solution was obtained. 5 PTCA balloon catheters were sprayed or dipped in the solution, dried, and sprayed or dipped again until sufficient amount of drug on the balloon (3 microgram per square mm) is obtained. The coated balloon was then treated under high pH (range pH 8-11.5) conditions to hydrolyze the anhydride.

This can be confirmed by IR method. The hydrophilicity of the coating was now increased. The coated balloons were then sterilized for animal test.

Example 12

The drug coated balloon catheters and uncoated balloon catheters (as control) were inserted via a bronchoscope into the pulmonary airway in pigs. The balloon was dilated, and the inflated balloon was held expanded in the lumen for 60 seconds to release drug and additive. The balloon was deflated and withdrawn from the pig. The animals were then examined bronchoscopically and tissues samples were taken for pathology and quantification of drug uptake after 3 days, 31 days, 3 months, 6 months, 9 months and 12 months.

Example 13

The uncoated stent delivery catheters were inserted into the vascular lumen in pigs. The balloon was dilated, the stent was deployed and the deflated balloon was the withdrawn. The pharmaceutical formulation 1-15 of example 1 (10-100 ml) was injected (about 5-15 mg drug per pig) at the site of stent implantation. The drug was then absorbed by injured tissue. The animals were then examined and tissues samples were taken for pathology.

Example 14

The diseased tissue (breast cancer or prostate or atheroma or stenosis) was removed surgically from a human body. The pharmaceutical formulation 1-15 of example 1 (10-100 ml) was then injected into or onto the surgical cavities created by the surgical intervention (about 5-20 mg drug). The local drug delivery included injection by long needle, guide catheters, introducer shealth, drug infusion tube and other drug delivery catheters. The drug was then absorbed by tissue at the target site.

Example 15

6 PTCA balloon catheters (3.5 and 3.0 mm in diameter and 20 mm in length) were inflated at 1-3 atm. The inflated balloon was loaded with a formulation 18-28 in example 1. A sufficient amount of drug on the balloon (3 microgram per square mm) was obtained. The inflated balloon was folded, and then dried. The coated folded balloon was then rewrapped and sterilized for animal testing.

The coated PTCA balloon catheter was inserted into a target site in the coronary vasculature (LAD, LCX and RCA) of a 25-45 pound pig. The balloon was inflated to about 12 atm. The overstretch ratio (the ratio of balloon diameter to vessel diameter) was about 1.15-1.20. The drug delivered into the target tissue during 30-60 seconds of inflation. The balloon catheter was then deflated and was withdrawn from animal body. The target blood vessel was harvested 0.25-24 hours after the procedure. The drug content in the target tissue and the residual drug remaining on the balloon were analyzed by tissue extraction and HPLC.

In some of these animal studies, a stent was crimped on the drug coated balloon catheters prior to deployment. In chronic animal tests, angiography was performed before and after all interventions and at 28-35 days after the procedure. Luminal diameters were measured and late lumen loss was calculated. Late lumen loss is the difference between the minimal lumen diameter measured after a period of follow-up time (usually weeks to months after an intervention, such as angioplasty and stent placement in the case of this example) and the minimal lumen diameter measured immediately after the intervention. Restenosis may be quantified by the diameter stenosis, which is the difference between the mean lumen diameters at follow-up and immediately after the procedure divided by the mean lumen diameter immediately after the procedure. The animal test results for Formulations 18-28 are reported below. All data is an average of five or six experimental data points.

The drug content of the formulation 18 on the 3.5 mm balloon catheters was 3.26 µg/mm$^2$. After the procedure, the residual drug on the balloon was 15.92 µg, or 2.3% of the total drug loaded on the balloon. The drug content in tissue harvested 15-30 minutes after the procedure was 64.79 µg, or 9.2% of the total drug content originally loaded on the balloon. When an 18 mm stent was deployed by the coated balloon, the residual drug on the balloon was 31.96 µg, or 4.5% of drug load, and the drug content in tissue harvested 15-30 minutes after the procedure was 96.49 µg, or 13.7% of drug load. The stretch ratio is 1.3 in the procedure. The late lumen loss after 28-35 days was 0.10 (sd 0.2) mm. The diameter stenosis is 3.3%.

The drug content of the formulation 19 on the 3.5 mm balloon catheters was 3.08 µg/mm$^2$. After the procedure, the residual drug on the balloon was 80.58 µg, or 11.4% of the total drug load. The drug content in tissue harvested 15-30 minutes after the procedure was 42.23 µg, or 6.0% of the total drug load. After 28-35 days late lumen loss was 0.30 (sd 0.23) mm. The diameter stenosis was 5.4%.

The drug content of formulation 20 on the 3.5 mm balloon catheters was 3.61 µg/mm$^2$. After the procedure, the residual drug on the balloon was 174.24 µg, or 24.7% of the total drug load. The drug content in tissue harvested 15-30 minutes after the procedure was 83.83 µg, or 11.9% of the total drug load. When deployed with a pre-crimped 18 mm stent, the residual drug on the balloon is 114.53 µg, or 16.1% of the total drug load, and the drug content in tissue harvested 15-30 minutes post procedure was 147.95 µg, or 18.1% of the total drug load. The stretch ratio was 1.3 in the procedure. The late lumen loss after 28-35 days was 0.10 (sd 0.1) mm. The diameter stenosis was 3.4%.

The drug content of formulation 21 on the 3.5 mm balloon catheters was 4.71 µg/mm$^2$. After the procedure, the residual drug on the balloon was 44.39 µg, or 6.3% of the total drug load. The drug content in the tissue harvested 15-30 minutes after the procedure was 77.87 µg, or 11.0% of the total drug load. After 28-35 days late lumen loss was 0.23 (sd 0.44) mm. The diameter stenosis was 7.3%.

The drug content of the formulation 22 on the 3.5 mm balloon catheters was 3.85 µg/mm$^2$. After the procedure, residual drug on the balloon was 24.59 µg, or 3.5% of the total drug load. The drug content in tissue harvested 15-30 minutes after the procedure was 37.97 µg, or 5.4% of the total drug load. After 28-35 days late lumen loss was 0.33 (sd 0.14) mm. The diameter stenosis was 6.7%.

The drug content of formulation 23 on the 3.5 mm balloon catheters was 3.75 µg/mm$^2$. After the procedure, residual drug on the balloon was 0.82 µg, or 0.1% of the total drug load. The drug content in tissue harvested 60 minutes after the procedure was 45.23 µg, or 5.5% of the total drug load. After 28-35 days late lumen loss was 0.49 (sd 0.26) mm. The diameter stenosis was 11.3%.

The drug content of formulation 24 on the 3.5 mm balloon catheters was 3.35 µg/mm$^2$. After the procedure, the residual drug on the balloon was 62.07 µg, or 7.5% of the total drug load. The drug content in tissue harvested 60 minutes after the procedure was 40.55 µg, or 4.9% of the total drug load. After 28-35 days late lumen loss was 0.47 (sd 0.33) mm. The diameter stenosis was 9.9%.

The drug content of the formulation 25 on the 3.5 mm balloon catheters was 3.41 µg/mm². After the procedure, residual drug on the balloon was 50.0 µg, or 6.0% of the total drug load. The drug content in tissue harvested 60 minutes post procedure was 26.72 µg, or 3.2% of the total drug load. After 28-35 days late lumen loss was 0.36 (sd 0.41) mm. The diameter stenosis was 9.3%.

The drug content of formulation 28 on the 3.5 mm balloon catheters was 3.10 µg/mm². After the procedure, residual drug on the balloon was 1.9% of the total drug load. The drug content in tissue harvested 2 hours after the procedure was 34.17 µg, or 5.0% of the total drug load. In tissue harvested 24 hours after the procedure, the drug content in tissue was 28.92 µg, or 4.2% of the total drug load.

The drug content of control formulation (uncoated balloon) on the 3.5 mm balloon catheters was 0.0 µg/mm². After the procedure, residual drug on the balloon was 0% of the total drug load. The drug content in tissue harvested 15 minutes after the procedure was 0 µg. In tissue harvested 24 hours after the procedure, the drug content in tissue was 0 µg. after 28-35 days late lumen loss was 0.67 (sd 0.27) mm. The diameter stenosis is 20.8%. In the second repeat experiment, the stretch ratio was 1.3. The late lumen loss was 1.1 (sd 0.1). The diameter stenosis was 37.5%.

The drug content of the comparison formulation 26 on the 3.5 mm balloon catheters was 3.21 µg/mm². After the procedure, residual drug on the balloon was 13.52 µg, or 1.9% of the total drug load. The drug content in the tissue was 28.32 µg, or 4.0% of the total drug load. When the balloon was deployed with a pre-crimped 18 mm stent, residual drug on the balloon was 26.45 µg, or 3.7% of the total drug load. The drug content in tissue was 113.79 µg, or 16.1% of drug load. After 28-35 days, late lumen loss was 0.27 (sd 0.15) mm. The diameter stenosis was 7.1%.

The drug content of the formulation 27 (without additive) on the 3.5 mm balloon catheters was 4.22 µg/mm². After the procedure, residual drug on the balloon was 321.97 µg, or 45.6% of the total drug load. The drug content in the tissue was 12.83 µg, or 1.8% of the total drug load.

Suprisingly, the concentration of drug absorbed by porcine coronary artery tissue after deployment of balloons coated with formulations 18-25 and 28 according to embodiments of the present invention was higher than that delivered by balloons coated with the comparison formulation 26 and higher than those coated with drug alone, formulation 27. The late lumen loss after 28-35 days follow up was less than the control (uncoated balloon).

Example 16

6 PTCA balloon catheters (3.5 and 3.0 mm in diameter and 20 mm in length) were inflated at 1-3 atm. The inflated balloon was loaded with a formulation 18-25, and 28 in example 1. A sufficient amount (3 µg/mm²) of drug on the balloon surface was obtained. The inflated balloon was dried. The drug coated balloon was then loaded with a top coat. The top coating formulation in acetone or ethanol was chosen from gentisic acid, methyl paraben, acetic acid, Tween 20, vanillin and aspirin. The coated folded balloon was dried, then rewrapped and sterilized for animal testing.

A floating experiment was designed to test how much drug is lost during balloon catheter insertion and transit to the target site prior to inflation. A control balloon catheter was coated with formulation 18. Top-coated catheters also were prepared having a top coating of propyl paraben. For top-coated catheters, the balloon catheter was coated with formulation 18, then dried, 25-50 mg propyl paraben (about 50% of paclitaxel by weight) in acetone was coated over the formulation 18 coating. Each of the control and top-coated balloon catheters was inserted in pig arteries. The floating time in pig arterial vasculature was 1 minute. The drug, additive and top coating were released. The catheter was then withdrawn. The residual drug on the balloon catheters was analyzed by HPLC. The residual drug content of the control balloon catheters was 53% of the total drug loading. The residual drug content of the top-coated balloon catheter was 88%. The top coat reduced drug loss in the vasculature during conditions that simulate transit of the device to a site of therapeutic intervention. The same animal tests were performed as in Example 15 with formulation 18 first coated on the balloon, and propyl paraben as a top coating layer overlying the first coating layer. The drug content on the 3.5 mm balloon catheter was 3.39 µg/mm². After the procedure, residual drug on the balloon was 64.5 µg, or 8.6% of the total drug load. The drug content in the tissue was 28.42 µg, or 4% of the total drug load.

Example 17

6 PTCA balloon components (3.5 and 3.0 mm in diameter and 20 mm in length) were loaded with formulation 18 provided in Example 1. A sufficient amount of drug (3 µg/mm²) was obtained on the balloon surface. The balloon was dried.

A formulation for a top coating layer was then prepared. The formulation of the top coating layer was paclitaxel, and one additive chosen from Tween 20, Tween 80, polypropylene glycol-425 (PPG-425), and polypropyl glycol-1000 (PPG-1000), in acetone. The balloon surface of the control catheters was only loaded with formulation 18. 25-50 mg of the top coating formulation (about 50% of paclitaxel by weight) in acetone was coated over the formulation 18 coating layer on the other balloon surfaces. The coated balloons were dried for drug releasing testing in vitro.

The releasing experiment was designed to test how much drug is lost during balloon inflation. Each of the coated balloons were inflated to 12 atm. in 1% BSA solution at 37° C. for 2 minutes. The drug, additive and top coating were released. The residual drug on the balloon catheters was analyzed by HPLC. The residual drug content of the control balloon catheter was 34% of the total drug loading. The residual drug content of the balloon catheter that included a top coating layer with Tween 20, Tween 80, polypropylene glycol-425 (PPG-425) or polypropyl glycol-1000 (PPG-1000) was 47%, 56%, 71% and 81%, respectively. Thus, the top coating layer reduced drug loss in the tests in vitro during inflation of the balloon components.

What is claimed is:
1. A balloon catheter for delivering a therapeutic agent to target site in a blood vessel, the balloon catheter comprising:
   a coating layer overlying an exterior surface of a balloon, the coating layer comprising a therapeutic agent and at least one first additive, wherein:
      the therapeutic agent is selected from the group consisting of paclitaxel, rapamycin, and combinations thereof; and
      the at least one first additive comprises a PEG fatty ester selected from the group consisting of PEG laurates, PEG oleates, PEG stearates, PEG glyceryl laurates, PEG glyceryl oleates, PEG glyceryl stearates, PEG sorbitan monolaurates, PEG sorbitan monooleates,

PEG sorbitan stearates, PEG sorbitan laurates, PEG sorbitan oleates, PEG sorbitan palmitates, and combinations thereof; and an adherent layer between the coating layer and the exterior surface of the balloon, the adherent layer comprising a biocompatible polymer selected from the group consisting of polyolefins, polyisobutylene, ethylene-1-olefin copolymers, acrylic polymers, polyvinyl chloride, polyvinyl methyl ether, polyvinylidene fluoride, polyvinylidene chloride, polyacrylonitrile, polyvinyl ketones, polystyrene, polyvinyl acetate, ethylene-methyl methacrylate copolymers, acrylonitrile-styrene copolymers, ABS resins, Nylon 12, polycaprolactone, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, silicones, ethylene vinyl acetate copolymers, EPDM rubbers, and mixtures and block copolymers thereof.

2. The balloon catheter of claim 1, wherein the adherent layer does not contain a therapeutic agent.

3. The balloon catheter of claim 1, wherein the at least one first additive is selected from the group consisting of PEG-20 sorbitan monolaurate, PEG-20 sorbitan monopalmitate, PEG-20 sorbitan monostearate, PEG-20 sorbitan monooleate, and combinations thereof.

4. The balloon catheter of claim 1, wherein the at least one first additive is selected from the group consisting of PEG-20 sorbitan monolaurate, PEG-20 sorbitan monooleate, and combinations thereof.

5. The balloon catheter of claim 1, wherein the coating layer further comprises a second additive selected from the group consisting of polyglyceryl-10 oleate, octoxynol-9, p-isononylphenoxypolyglycidol, Tyloxapol, niacinamide, nicotinic acid, thiamine hydrochloride, 2-pyrrolidone-5-carboxylic acid, gluconolactone, sorbitol, meglumine, lactobionic acid, N-octanoyl-N-methylglucamine, lactic acid, gensitic acid, diethanolamine, and combinations thereof.

6. The balloon catheter of claim 5, wherein the second additive is selected from the group consisting of polyglyceryl-10 oleate, p-isononylphenoxypolyglycidol, gluconolactone, sorbitol, lactobionic acid, N-octanoyl-N-methylglucamine, and combinations thereof.

7. The balloon catheter of claim 5, wherein the second additive is selected from the group consisting of gluconolactone, sorbitol, lactobionic acid, N-octanoyl-N-methylglucamine, and combinations thereof.

8. The balloon catheter of claim 5, wherein the second additive is selected from the group consisting of gluconolactone, sorbitol, and combinations thereof.

9. The balloon catheter of claim 5, wherein the at least one first additive is PEG-20 sorbitan monolaurate and the second additive is selected from the group consisting of gluconolactone, sorbitol, lactobionic acid, N-octanoyl-N-methylglucamine, and combinations thereof.

10. The balloon catheter of claim 5, wherein the at least one first additive is PEG-20 sorbitan monolaurate, and the second additive is selected from the group consisting of gluconolactone, sorbitol and combinations thereof.

11. The balloon catheter of claim 5, wherein the therapeutic agent is paclitaxel, the at least one first additive is PEG-20 sorbitan monolaurate, and the second additive is selected from the group consisting of gluconolactone, sorbitol, and combinations thereof.

12. The balloon catheter of claim 5, wherein the therapeutic agent is paclitaxel, the at least one first additive is PEG-20 sorbitan monolaurate, and the second additive is gluconolactone.

13. The balloon catheter of claim 5, wherein the therapeutic agent is paclitaxel, the at least one first additive is PEG-20 sorbitan monolaurate, and the second additive is sorbitol.

14. The balloon catheter of claim 1, wherein the catheter further comprises a dimethylsulfoxide solvent layer overlying the surface of the coating layer.

15. The balloon catheter of claim 1, wherein the coating layer further comprises a second therapeutic agent selected from the group consisting of beta-lapachone and biologically active vitamin D.

16. The balloon catheter of claim 1, wherein the concentration of the therapeutic agent in the coating layer is from 1 to 20 $\mu g/mm^2$.

17. The balloon catheter of claim 1, wherein the concentration of the therapeutic agent in the coating layer is from 2 to 10 $\mu g/mm^2$.

18. The balloon catheter of claim 1, wherein the ratio by weight of the at least one first additive to the therapeutic agent in the coating layer is from about 0.1 to 5.

19. The balloon catheter of claim 1, wherein the ratio by weight of the at least one first additive to the therapeutic agent in the coating layer is from about 0.5 to 2.

20. The balloon catheter of claim 1, wherein the ratio by weight of the at least one first additive to the therapeutic agent in the coating layer is from about 0.8 to 1.2.

21. The balloon catheter of claim 1, wherein the coating layer does not include an iodine covalent bonded contrast agent.

22. The balloon catheter of claim 1, wherein the at least one first additive is not a therapeutic agent.

23. The balloon catheter of claim 1, wherein the at least one first additive is not salicylic acid or salts thereof.

24. The balloon catheter of claim 1, wherein the coating layer does not include oil.

25. The balloon catheter of claim 1, wherein the therapeutic agent is not enclosed in micelles or encapsulated in polymer particles.

26. The balloon catheter of claim 25, wherein the coating layer does not include a polymer.

27. The balloon catheter of claim 1, further comprising a top layer overlying the surface of the coating layer, wherein the top layer comprises an additive that is less hydrophilic than the at least one first additive in the coating layer, and wherein the additive in the top layer is selected from the group consisting of p-isononylphenoxypolyglycidol, PEG-20 sorbitan monolaurate, PEG-20 sorbitan monopalmitate, PEG-20 monostearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, polyglyceryl-6 oleate, polyglyceryl-6 myristate, polyglyceryl-6 palmitate, polyglyceryl-10 laurate, polyglyceryl-10 oleate, polyglyceryl-10 myristate, polyglyceryl-10 palmitate, PEG sorbitan monolaurate, PEG sorbitan monolaurate, PEG sorbitan monooleate, PEG oleyl ether, PEG lauryl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside, cystine, tyrosine, tryptophan, leucine, isoleucine, phenylalanine, asparagine, aspartic acid, glutamic acid, methionine, ascorbic acid, 2-pyrrolidone-5-carboxylic acid, sodium pyrrolidone carboxylate, ethylenediaminetetraacetic dianhydride, cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin U, albumin, benzalkonium chloride, benzethonium chloride, docecyl trimethyl ammonium bromide, sodium dodecylsulfates, dialkyl methylbenzyl ammonium chloride, dialkylesters of sodium sulfonsuccinic acid, L-ascorbic acid and its salts, D-glucoascorbic acid and its salts, tromethamine, triethanolamine, diethanolamine, meglumine, glucamine, amine alcohols, glucoheptonic acid, gluconic acid, hydroxy ketones, hydroxy lactones, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactitol, sinapic acid, vanillic acid, vanillin, methyl paraben, propyl paraben, sorbitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, and combinations thereof.

28. The balloon catheter of claim 27, wherein the additive in the top layer is selected from the group consisting of PEG-20 sorbitan monolaurate, PEG-20 sorbitan monopalmitate, PEG-20 monostearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, polyglyceryl-6 oleate, polyglyceryl-6 myristate, polyglyceryl-6 palmitate, polyglyceryl-10 laurate, polyglyceryl-10 oleate, polyglyceryl-10 myristate, and polyglyceryl-10 palmitate.

29. The balloon catheter of claim 27, wherein the top layer further comprises a therapeutic agent selected from the group consisting of paclitaxel, rapamycin, or combinations thereof.

30. The balloon catheter of claim 29, wherein the concentration of the therapeutic agent in the top layer is lower than the concentration of the therapeutic agent in the coating layer.

* * * * *